United States Patent
Aoyama

(10) Patent No.: US 12,131,479 B2
(45) Date of Patent: Oct. 29, 2024

(54) MEDICAL IMAGE PROCESSING APPARATUS, SYSTEM, AND METHOD

(71) Applicant: CANON MEDICAL SYSTEMS CORPORATION, Otawara (JP)

(72) Inventor: Gakuto Aoyama, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 450 days.

(21) Appl. No.: 17/392,657

(22) Filed: Aug. 3, 2021

(65) Prior Publication Data
US 2022/0044408 A1    Feb. 10, 2022

(30) Foreign Application Priority Data

Aug. 7, 2020 (JP) .................................. 2020-134898
Jul. 27, 2021 (JP) .................................. 2021-122384

(51) Int. Cl.
*G06T 7/11* (2017.01)

(52) U.S. Cl.
CPC ...... *G06T 7/11* (2017.01); *G06T 2207/10081* (2013.01); *G06T 2207/30101* (2013.01); *G06T 2207/30172* (2013.01)

(58) Field of Classification Search
CPC ... A61B 5/02007; A61B 5/1075; A61B 6/503; A61B 6/5217; A61B 2576/023; G06T 7/11; G06T 2207/10081; G06T 2207/30101; G06T 2207/30172
See application file for complete search history.

(56) References Cited

U.S. PATENT DOCUMENTS

| 7,751,984 B2 * | 7/2010 | Tang ...................... G16H 30/40 382/128 |
| 9,984,465 B1 * | 5/2018 | Ma ............................ G06T 7/32 |
| 11,727,570 B2 * | 8/2023 | Samady ............... A61B 8/0891 |

(Continued)

FOREIGN PATENT DOCUMENTS

| JP | 2011-062358 A | 3/2011 |
| JP | 2016-533815 A | 11/2016 |

(Continued)

OTHER PUBLICATIONS

Eshtehard et al. "High wall shear stress and high-risk plaque: an emerging concept." The international journal of cardiovascular imaging 33 (2017): 1089-1099. (Year: 2017).*

(Continued)

*Primary Examiner* — Katrina R Fujita
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry acquires the distribution of the wall shear stress of a blood vessel. The processing circuitry extracts a representative value or a blood vessel region from the distribution of the wall shear stress in the blood vessel on the basis of an extraction criterion determined for each region in accordance with the shape or the property of the blood vessel. The processing circuitry changes the display mode of the wall shear stress in the blood vessel on the basis of a result of extracting the representative value of the wall shear stress or a characteristic blood vessel region.

29 Claims, 18 Drawing Sheets

(56) References Cited

U.S. PATENT DOCUMENTS

| | | | | |
|---|---|---|---|---|
| 11,813,104 | B2* | 11/2023 | Samady | A61B 6/5217 |
| 2010/0053160 | A1* | 3/2010 | Arakita | G06T 3/0037 |
| | | | | 382/131 |
| 2011/0275936 | A1* | 11/2011 | Cho | A61B 8/485 |
| | | | | 600/438 |
| 2015/0348247 | A1* | 12/2015 | Mclaughlin | G06T 5/40 |
| | | | | 382/131 |
| 2016/0203288 | A1* | 7/2016 | Meng | G06T 7/11 |
| | | | | 703/2 |
| 2017/0017771 | A1* | 1/2017 | Koo | A61B 5/0215 |
| 2017/0095221 | A1* | 4/2017 | Kato | G16H 30/40 |
| 2017/0124701 | A1* | 5/2017 | Liang | A61B 8/5223 |
| 2017/0245821 | A1* | 8/2017 | Itu | G06F 18/2413 |
| 2018/0211387 | A1* | 7/2018 | Wang | A61B 5/02007 |
| 2019/0336096 | A1* | 11/2019 | Itu | G16H 50/50 |
| 2020/0105420 | A1* | 4/2020 | Malota | G16H 50/50 |
| 2020/0126219 | A1 | 4/2020 | Wang et al. | |
| 2020/0222018 | A1* | 7/2020 | Van Walsum | A61B 6/463 |
| 2021/0236086 | A1* | 8/2021 | Du | A61B 8/0891 |
| 2021/0244475 | A1* | 8/2021 | Taylor | A61B 6/5217 |

FOREIGN PATENT DOCUMENTS

| | | |
|---|---|---|
| JP | 2020-518362 A | 6/2020 |
| WO | WO 2015/023495 A1 | 2/2015 |

OTHER PUBLICATIONS

Hoogendoorn et al. "Multidirectional wall shear stress promotes advanced coronary plaque development: comparing five shear stress metrics." Cardiovascular research 116.6 (2020): 1136-1146. (Year: 2020).*

Kumar et al. "High coronary shear stress in patients with coronary artery disease predicts myocardial infarction." Journal of the American College of Cardiology 72.16 (2018): 1926-1935. (Year: 2018).*

Murata et al. "High shear stress on the coronary arterial wall is related to computed tomography-derived high-risk plaque: a three-dimensional computed tomography and color-coded tissue-characterizing intravascular ultrasonography study." Heart and vessels 34 (2019): 1429-1439. (Year: 2019).*

Balocco et al. "Relation between plaque type, plaque thickness, blood shear stress, and plaque stress in coronary arteries assessed by X-ray Angiography and Intravascular Ultrasound." Medical Physics 39.12 (2012): 7430-7445. (Year: 2012).*

Oyre et al. "Quantitation of circumferential subpixel vessel wall position and wall shear stress by multiple sectored three-dimensional paraboloid modeling of velocity encoded cine MR." Magnetic resonance in medicine 40.5 (1998): 645-655. (Year: 1998).*

Wahle et al. "Plaque development, vessel curvature, and wall shear stress in coronary arteries assessed by X-ray angiography and intravascular ultrasound." Medical image analysis 10.4 (2006): 615-631. (Year: 2006).*

* cited by examiner

FIG.3
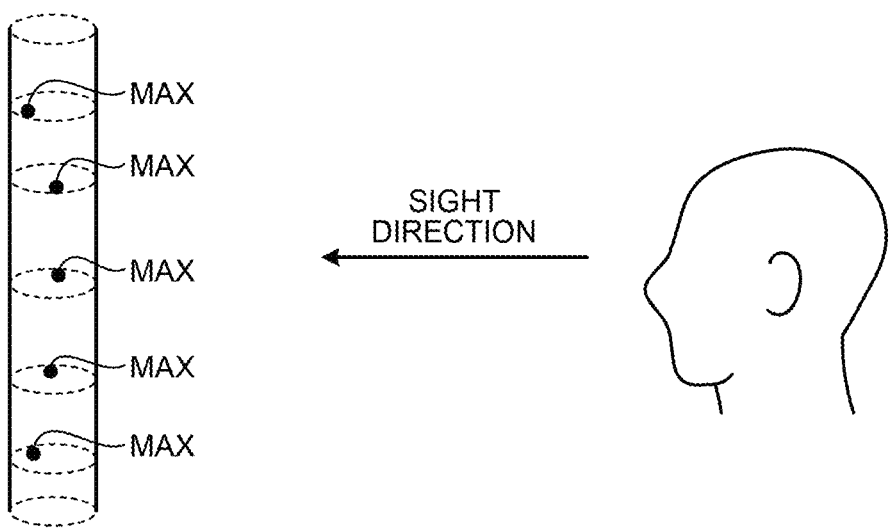
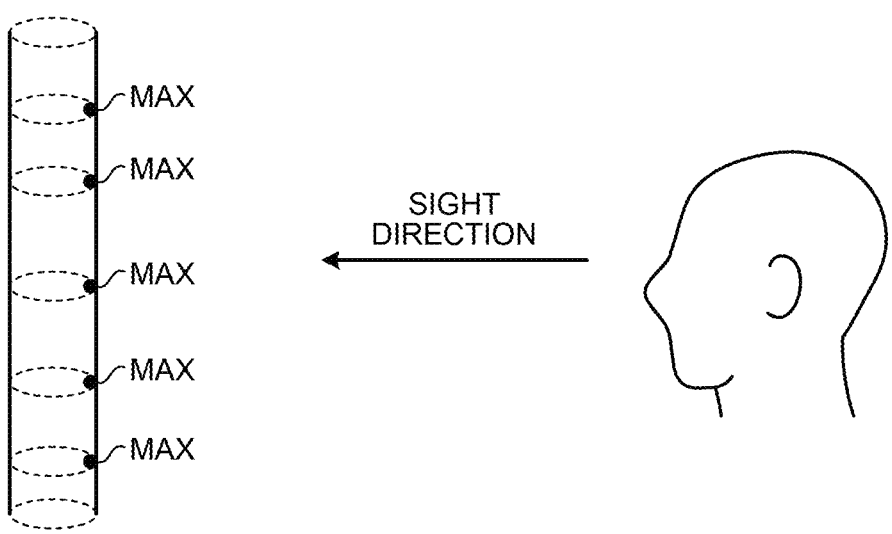

FIG.5
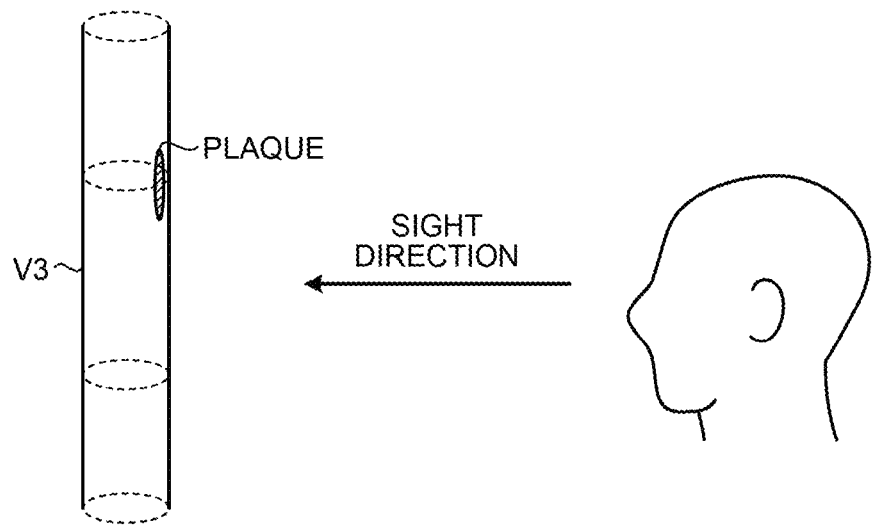
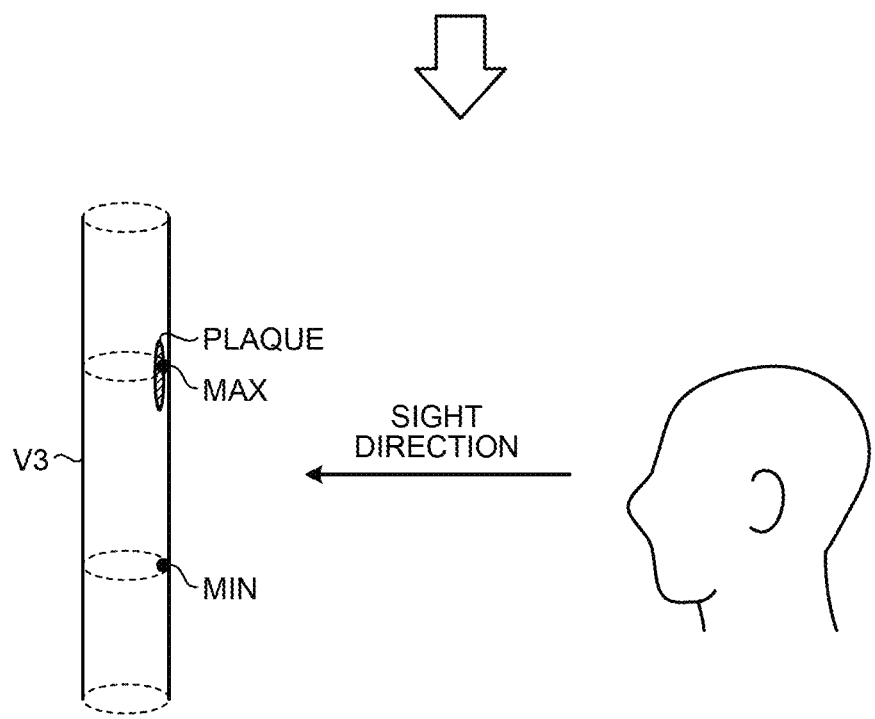

FIG.10
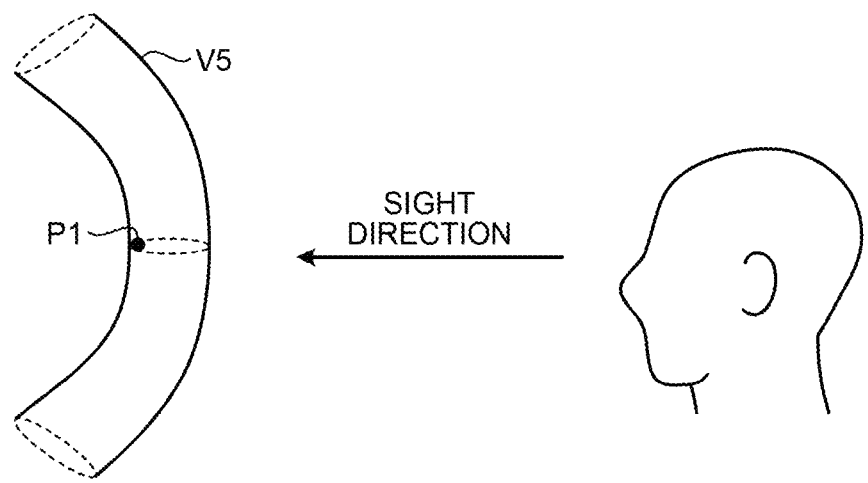
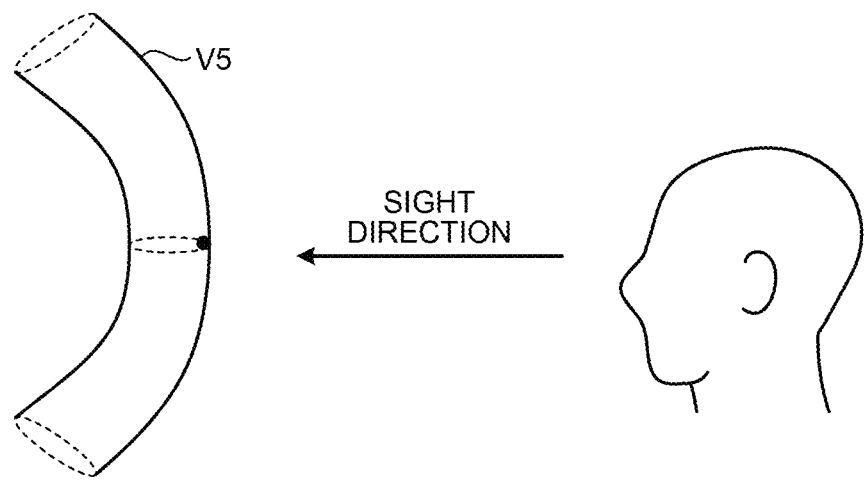

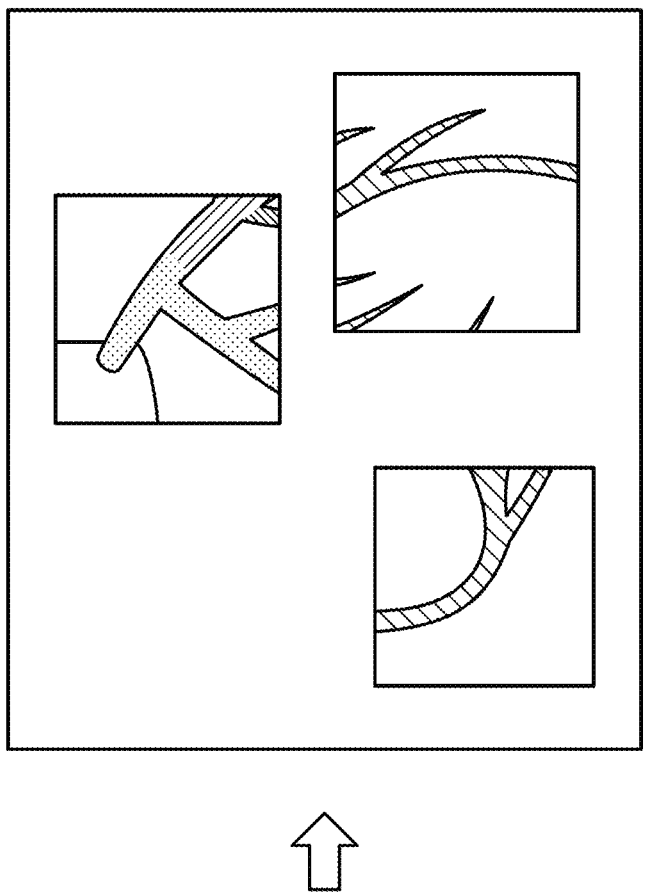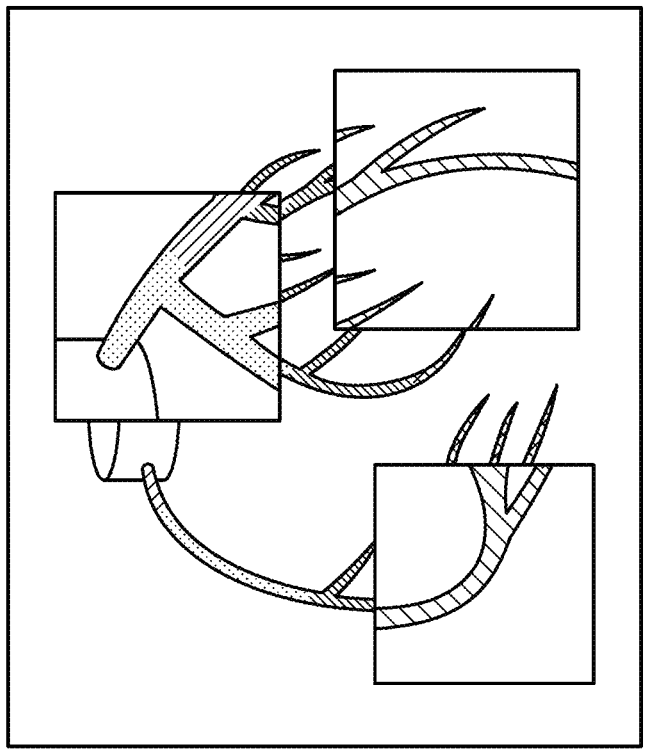
FIG.16

MEDICAL IMAGE PROCESSING APPARATUS, SYSTEM, AND METHOD

CROSS-REFERENCE TO RELATED APPLICATIONS

This application is based upon and claims the benefit of priority from Japanese Patent Application No. 2020-134898, filed on Aug. 7, 2020; and Japanese Patent Application No. 2021-122384, filed on Jul. 27, 2021, the entire contents of all of which are incorporated herein by reference.

FIELD

Embodiments disclosed in the present specification and the drawings relate to medical image processing apparatus, system, and method.

BACKGROUND

In one example of the conventionally known techniques for supporting the diagnosis or planning the treatment schedule about heart diseases, various kinds of information about the bloodstream of a blood vessel of a subject's heart is presented on the basis of a medical image about the blood vessel of the heart. One example of the information about the bloodstream is wall shear stress (WSS) at each position in the blood vessel and this WSS is calculated and displayed.

BRIEF DESCRIPTION OF THE DRAWINGS

FIG. 3 is a diagram for describing one example of an extracting process and a display controlling process in the first embodiment;

FIG. 5 is a diagram for describing one example of the extracting process and the display controlling process in the first embodiment;

FIG. 10 is a diagram for describing one example of the extracting process and the display controlling process in a second embodiment;

FIG. 16 is a diagram illustrating one example of the display controlling process in the second embodiment;

DETAILED DESCRIPTION

Embodiments of medical image processing apparatus, system, and method are hereinafter described in detail with reference to the drawings. Note that the medical image processing apparatus, medical image processing system and the medical image processing method according to the present application are not limited by the embodiments below. Note that the embodiment can be combined with another embodiment or a conventional technique within the range where the content of the process does not contradict.

First Embodiment

Figure 1:
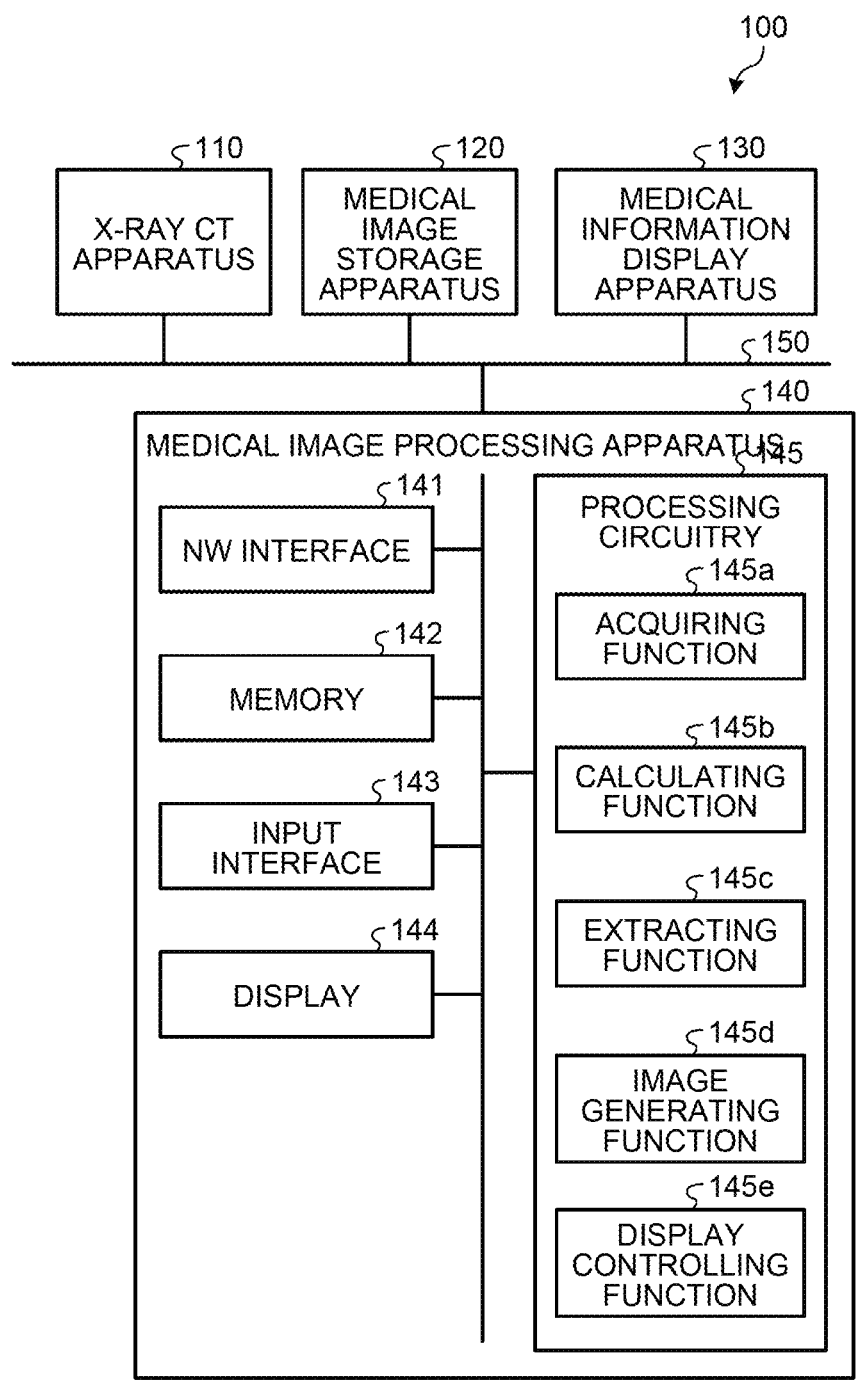
FIG. 1 is a diagram illustrating a structure example of a medical image processing system and a medical image processing apparatus according to a first embodiment.

FIG. 1 is a diagram illustrating a structure example of a medical image processing system and a medical image processing apparatus according to a first embodiment.

For example, as illustrated in FIG. 1, a medical image processing system 100 according to the present embodiment includes an X-ray computed tomography (CT) apparatus 110, a medical image storage apparatus 120, a medical information display apparatus 130, and a medical image processing apparatus 140. Here, the respective apparatuses and the system are connected through a network 150 so that communication is possible.

Note that, in addition to the X-ray CT apparatus 110, the medical image processing system 100 may include another medical image diagnosis apparatus such as a magnetic resonance imaging (MRI) apparatus, an ultrasonic diagnosis apparatus, a positron emission tomography (PET) apparatus, or a single photon emission computed tomography (SPECT) apparatus. Furthermore, the medical image processing system 100 may include another system such as an electronic medical record system, a hospital information system (HIS), or a radiology information system (RIS).

The X-ray CT apparatus 110 generates a CT image about a subject. Specifically, the X-ray CT apparatus 110 collects projection data expressing the distribution of X-rays having transmitted a subject by turning and moving an X-ray tube and an X-ray detector on a circular orbit surrounding a subject. Then, the X-ray CT apparatus 110 generates a CT image on the basis of the collected projection data.

The medical image storage apparatus 120 keeps various kinds of medical images about the subject. Specifically, the medical image storage apparatus 120 acquires a CT image from the X-ray CT apparatus 110 through the network 150, stores the CT image in a memory in the medical image storage apparatus 120, and keeps the CT image. For example, the medical image storage apparatus 120 is achieved by a computer apparatus such as a server or a work station. Alternatively, the medical image storage apparatus 120 is achieved by a picture archiving and communication system (PACS) or the like, and keeps the CT image in a format based on digital imaging and communications in medicine (DICOM).

The medical information display apparatus 130 displays various kinds of medical information about a subject. Specifically, the medical information display apparatus 130 acquires the medical information including the CT images and the processing results of the image processing from the medical image storage apparatus 120 through the network 150, and causes the display in the medical information display apparatus 130 to display the acquired medical information. For example, the medical information display apparatus 130 is achieved by a computer apparatus such as a work station, a personal computer, or a tablet terminal.

The medical image processing apparatus 140 performs various kinds of image processing about the subject. Specifically, the medical image processing apparatus 140 acquires the CT image from the X-ray CT apparatus 110 or the medical image storage apparatus 120 through the network 150, and performs various kinds of image processing using the acquired CT image. For example, the medical image processing apparatus 140 is achieved by a computer apparatus such as a server or a work station.

For example, the medical image processing apparatus 140 includes a network (NW) interface 141, a memory 142, an input interface 143, a display 144, and processing circuitry 145.

The NW interface 141 controls the transmission and communication of various kinds of data to be exchanged between the medical image processing apparatus 140 and another apparatus connected through the network 150. Specifically, the NW interface 141 is connected to the processing circuitry 145, and transmits the data received from another apparatus to the processing circuitry 145, or transmits the data received from the processing circuitry 145 to another apparatus. For example, the NW interface 141 is achieved by a network card, a network adaptor, a network interface controller (NIC), or the like.

The memory 142 stores various kinds of data and various kinds of computer programs. Specifically, the memory 142 is connected to the processing circuitry 145, and stores the data received from the processing circuitry 145, or reads out the stored data and transmits the data to the processing circuitry 145. For example, the memory 142 is achieved by a semiconductor memory element such as a random access memory (RAM) or a flash memory, a hard disk, an optical disk, or the like.

The input interface 143 receives the input operation of various kinds of instructions and various kinds of information from a user. Specifically, the input interface 143 is connected to the processing circuitry 145, and converts the input operation received from the user into an electric signal and transmits the electric signal to the processing circuitry 145. For example, the input interface 143 is achieved by a trackball, a switch button, a mouse, a keyboard, a touch pad where input operation is performed by a touch on a screen, a touch screen combining the display screen and the touch pad, a non-contact input interface using an optical sensor, a voice-input interface, or the like. Note that in the present specification, the input interface 143 is not limited to only the input interface including the physical component such as a mouse or a keyboard. For example, a processing circuit for an electric signal that receives an electric signal corresponding to the input operation from an external input apparatus provided separately from the apparatus, and transmits this electric signal to the control circuit is also included in the examples of the input interface 143.

The display 144 displays various kinds of information and various kinds of data. Specifically, the display 144 is connected to the processing circuitry 145, and displays various kinds of information and various kinds of data received from the processing circuitry 145. For example, the display 144 is achieved by a liquid crystal monitor, a cathode ray tube (CRT) monitor, a touch panel, or the like.

The processing circuitry 145 controls the entire medical image processing apparatus 140. For example, the processing circuitry 145 performs various kinds of processes in accordance with the input operation received from the user through the input interface 143. For example, the processing circuitry 145 receives the data transmitted from another apparatus through the NW interface 141, and stores the received data in the memory 142. In addition, for example, the processing circuitry 145 transmits the data received from the memory 142 to the NW interface 141, thereby transmitting the data to another apparatus. Furthermore, for example, the processing circuitry 145 causes the display 144 to display the data received from the memory 142.

The structure examples of the medical image processing system 100 and the medical image processing apparatus 140 according to the present embodiment have been described. For example, the medical image processing system 100 and the medical image processing apparatus 140 according to the present embodiment are installed in medical facilities including hospitals and clinics, and support the diagnosis or planning the treatment schedule about heart diseases by the users including doctors.

Specifically, the medical image processing apparatus 140 calculates the wall shear stress (WSS) at each position in a blood vessel in the heart of the subject on the basis of the medical image about the blood vessel, and displays the wall shear stress. Here, the medical image processing apparatus 140 performs the display so that the wall shear stress is easily observed. That is to say, the medical image processing apparatus 140 performs the display so as to make it easier to see the WSS, so that the burden on the users including the doctors to read the WSS is reduced.

The WSS is calculated at each position on an inner wall of the blood vessel. That is to say, the WSS is index values distributed three-dimensionally throughout the blood vessel. On the other hand, since the display screen of the image display apparatus such as a display is two-dimensional, in the case of displaying the blood vessel as an image, the two-dimensional image viewed from a particular direction or the two-dimensional image taken along a particular cross section is displayed. In such a display screen, by displaying the image while continuously changing the particular direction of the two-dimensional image viewed from the particular direction, the three-dimensional structure of the blood vessel is expressed.

For example, coronary arteries are expressed as a three-dimensional structure by volume rendering (VR) display or surface rendering (SR) display, and on a screen at one time point, a two-dimensional coronary artery image observed from a particular direction is displayed. Therefore, in a case of mapping the WSS, which is calculated at each position in the blood vessel, on the coronary artery image in the VR display, some WSS can be observed (WSS on an observable region) and other WSS cannot be observed (WSS on an unobservable region).

Figure 2:
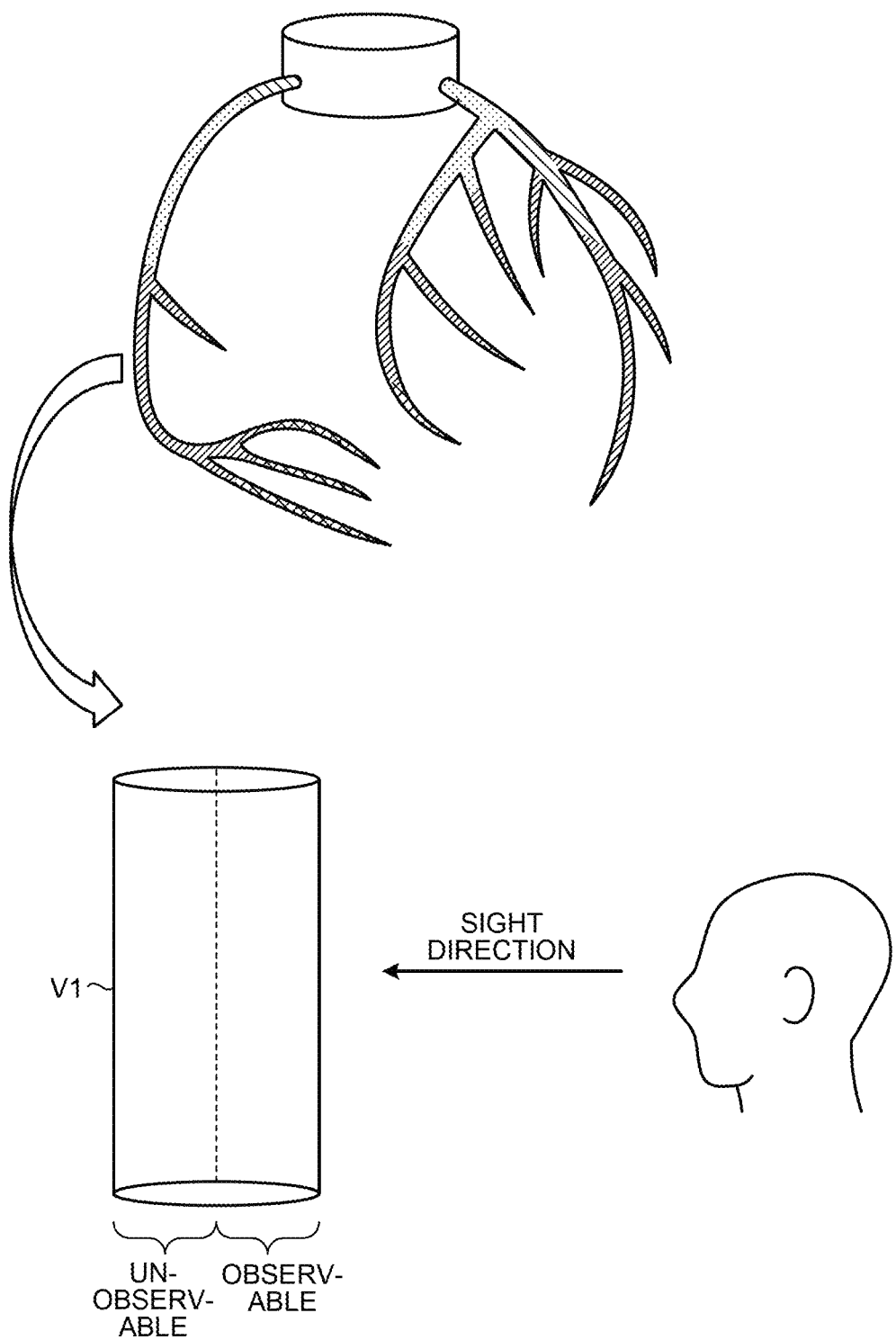
FIG. 2 is a diagram for describing a display example of WSS in the first embodiment.

FIG. 2 is a diagram for describing a display example of the WSS in the first embodiment. Here, FIG. 2 illustrates the observable region and the unobservable region in the case of observing the VR image of the coronary arteries. For example, calculating the WSS for the entire regions in a coronary artery V1 and displaying the calculated WSS mapped on the coronary artery V1 as illustrated in FIG. 2 can observe the WSS in the direction displayed on the screen (WSS on the front side of the screen) but cannot observe the WSS in the direction not displayed on the screen (WSS on the depth side of the screen).

Therefore, in the case where the WSS with an important characteristic exists on the depth side of the screen in such a display, the user may fail to find the characteristic WSS. In the case of observing the VR image by rotation, the user may fail to find the characteristic WSS unless observing the image by 360 degrees, and it takes time and effort.

In view of this, the medical image processing apparatus 140 according to the present embodiment is configured to display the WSS more clearly in a manner that the display region or the representative value of the WSS to be displayed is extracted based on the extraction criterion that is determined in accordance with the region, and thus reduce the burden on the users including the doctors when reading the WSS.

Specifically, the medical image processing apparatus 140 extracts the characteristic WSS or the characteristic region from each position in the blood vessel, and by changing the display mode of the WSS, displays the WSS more clearly.

The medical image processing apparatus 140 with such a structure is hereinafter described in detail. In the example to be described below, the coronary artery CT image is used as the medical image about the blood vessel.

For example, as illustrated in FIG. 1, in the present embodiment, the processing circuitry 145 in the medical image processing apparatus 140 performs an acquiring function 145a, a calculating function 145b, an extracting function 145c, an image generating function 145d, and a display controlling function 145e. Here, the calculating function 145b is one example of an acquisition unit. The extracting function 145c is one example of an extraction unit. The display controlling function 145e is one example of a display control unit.

The acquiring function 145a acquires the coronary artery CT image of the subject from the X-ray CT apparatus 110 or the medical image storage apparatus 120 through the NW interface 141. Specifically, the acquiring function 145a acquires the three-dimensional coronary artery CT image that can be used to calculate the WSS.

The calculating function 145b acquires the distribution of the wall shear stress of the blood vessel. For example, the calculating function 145b extracts a center line of the coronary artery included in the coronary artery CT image of the subject acquired by the acquiring function 145a. In addition, the calculating function 145b calculates the WSS on the basis of the coronary artery CT image of the subject acquired by the acquiring function 145a.

For example, the calculating function 145b calculates the WSS at each position in the coronary artery on the basis of the coronary artery CT image of the subject by a known method using computational fluid dynamics (CFD), machine learning, or the like.

The extracting function 145c extracts the representative value or the characteristic blood vessel region from the distribution of the WSS in the blood vessel on the basis of the extraction criterion determined for each region in accordance with the shape or the property of the blood vessel.

Specifically, the extracting function 145c calculates the value to be displayed from the spatial distribution of the WSS for each position along the center line of the blood vessel on the basis of the extraction criterion. Note that the process by the extracting function 145c is described below in detail.

The image generating function 145d generates various kinds of images for display. For example, the image generating function 145d generates the three-dimensional image of the coronary artery by reconstructing three-dimensionally the blood vessel region of the coronary artery in the coronary artery CT image. For example, the image generating function 145d generates a VR image, an SR image, a curved planer reconstruction (CPR) image, a multi planer reconstruction (MPR) image, a stretched multi planer reconstruction (SPR) image, or the like.

The display controlling function 145e changes the display mode of the wall shear stress in the blood vessel on the basis of the result of extracting the representative value of the wall shear stress or the characteristic blood vessel region. Specifically, the display controlling function 145e causes the display 144 to display the WSS according to the extraction result by the extracting function 145c. Note that the process by the display controlling function 145e is described below in detail.

The aforementioned processing circuitry 145 is achieved by a processor, for example. In this case, each of the aforementioned processing functions is stored in the memory 142 as a computer-executable computer program. Then, by reading and executing the computer program stored in the memory 142, the processing circuitry 145 achieves the function corresponding to each computer program. In other words, the processing circuitry 145 having read out each computer program has each processing function illustrated in FIG. 1.

Note that the processing circuitry 145 may be formed by combining a plurality of independent processors and may achieve each processing function when each processor executes the computer program. In addition, the respective processing functions of the processing circuitry 145 may be achieved dispersedly or integrally in one or a plurality of processing circuits as appropriate. The respective processing functions of the processing circuitry 145 may be achieved by a combination of hardware such as a circuit and software. Here, although the computer program corresponding to each processing function is stored in one memory 142 in this example, the embodiment is not limited to this example. As another example, the computer programs corresponding to the respective processing functions may be dispersedly stored in a plurality of memories and the processing circuitry 145 may read out each computer program from each memory and execute the computer program.

As described above, the medical image processing apparatus 140 extracts the characteristic WSS or the characteristic region from each position in the blood vessel, and changes the display mode of the WSS. One example of the process performed by the medical image processing apparatus 140 is described below.

Step 1

First, the medical image processing apparatus 140 acquires a three-dimensional medical image in the display of the WSS. Specifically, the acquiring function 145a acquires the coronary artery CT image of the subject from the X-ray CT apparatus 110 or the medical image storage apparatus 120 through the NW interface 141. More specifically, the acquiring function 145a acquires the three-dimensional coronary artery CT image that can be used to calculate the WSS. Note that the acquiring function 145a may acquire any kind of image based on which the shape of the blood vessel and the flow information including the flow rate of the blood can be calculated. For example, the acquiring function 145a can acquire the medical image (such as ultrasonic image or MRI image) collected by the medical image diagnosis apparatus other than the X-ray CT apparatus 110.

Step 2

Next, the medical image processing apparatus 140 extracts the center line of the blood vessel in the acquired three-dimensional medical image. Specifically, the calculating function 145b extracts the center line of the coronary artery included in the coronary artery CT image of the subject that is acquired by the acquiring function 145a. Here, the calculating function 145b can extract the center line of the coronary artery by known various methods including a method using a CT value.

Step 3

Then, the medical image processing apparatus 140 calculates the WSS from the acquired three-dimensional medical image. Specifically, the calculating function 145b calculates the WSS at each blood vessel position from the coronary artery CT image of the subject acquired by the acquiring function 145a in accordance with the known method using CFD, machine learning, or the like.

Step 4

After that, the medical image processing apparatus 140 calculates the representative value from the calculated WSS. Specifically, the extracting function 145c calculates the representative value of the WSS in the blood vessel on the basis of the extraction criterion determined for each region in accordance with the shape of the blood vessel. For example, the extracting function 145c calculates the characteristic value from all the WSS values at 360 degrees in the horizontally cross-sectional direction in which the center line is the axis, at each position of the center line of the coronary artery extracted by the calculating function 145b.

For example, the extracting function 145c calculates the highest value (maximum WSS) from among all the WSS values at 360 degrees in the horizontally cross-sectional direction in which the center line is the axis, as the representative value. Alternatively, the extracting function 145c can calculate the lowest value (minimum WSS) from among all the WSS values at 360 degrees in the horizontally cross-sectional direction in which the center line is the axis, as the representative value. Alternatively, as the representative value, the extracting function 145c can calculate the average value of all the WSS values at 360 degrees in the horizontally cross-sectional direction in which the center line is the axis. Further alternatively, the extracting function 145c can calculate the value of the WSS with the largest difference from the WSS at the vertically or horizontally adjacent blood vessel position (that is, the change quantity of WSS at the adjacent positions is large), as the representative value.

Step 5

Then, the medical image processing apparatus 140 causes a display apparatus, for example the display 144, to display the calculated WSS. Specifically, the image generating function 145d generates the three-dimensional display image including the blood vessel region in the three-dimensional medical image. For example, the image generating function 145d generates the display image such as a VR image or an SR image by reconstructing three-dimensionally the blood vessel region in the coronary artery CT image.

The display controlling function 145e performs the display of the WSS using the display image generated by the image generating function 145d. For example, the display controlling function 145e acquires the values of the WSS at all the positions in the blood vessel calculated by the calculating function 145b, and specifies the range where the WSS can exist on the basis of the maximum value and the minimum value of the acquired WSS values. Then, the display controlling function 145e sets the color arrangement (color lookup table) for the specified range, and assigns the color corresponding to the value of the WSS at each blood vessel position to each blood vessel position, thereby performing the display of a color image.

Step 6

Then, the medical image processing apparatus 140 changes the display mode of the WSS on the basis of the user's instruction. For example, the display controlling function 145e performs the display while switching between the normal display of the spatial distribution of the WSS and the display of the WSS based on the extraction result (calculation result) by the extracting function 145c in accordance with the user's switching operation (for example, selecting operation of switching button) through the input interface 143. In another example, the display controlling function 145e can control so that when the user performs the operation of rotating or browsing the image of the WSS, the WSS is normally displayed and when the operation stops, the WSS is displayed based on the extraction result (calculation result).

An example of extracting and displaying the representative value of the WSS is described below. In this case, the extracting function 145c calculates the maximum value, the minimum value, the average value, or the value with the largest difference from the adjacent value from the values of the WSS at the blood vessel wall intersecting with the cross section that is orthogonal to the center line of the blood vessel for each position of the center line. The display controlling function 145e changes the display mode of the WSS in the blood vessel so that the maximum value, the minimum value, the average value, or the value with the largest difference from the adjacent value that is calculated for each position of the center line of the blood vessel is displayed.

FIG. 3 is a diagram for describing one example of an extracting process and a display controlling process in the first embodiment. As illustrated in the diagram in an upper part of FIG. 3, the extracting function 145c calculates the maximum value as the characteristic WSS from all the WSS at 360 degrees in the horizontally cross-sectional direction in which the center line is the axis, at each position of the center line. That is to say, the extracting function 145c calculates the maximum value from the values of the WSS on each circle drawn with a dotted line for each position along the center line. Note that although FIG. 3 illustrates the example of calculating the maximum values about five positions, the maximum values are calculated about a number of positions along the center line of the blood vessel.

When the value of the characteristic WSS is calculated as described above, the display controlling function 145e changes the display mode of the WSS so that the calculated value is displayed. For example, in response to the user's instruction, the display controlling function 145e performs the display of a color image expressing the color corresponding to the maximum value of the WSS calculated at each position on the side of the coronary artery where the user can observe as illustrated in the diagram in a lower part of FIG. 3.

Note that although the maximum value of all the WSS in the horizontally cross-sectional direction at each position is calculated as the characteristic WSS in FIG. 3, the embodiment is not limited to this example, and the minimum value may be calculated or the average value of all the WSS in the horizontally cross-sectional direction may be calculated. Alternatively, the WSS with the largest difference from the WSS at the vertically or horizontally adjacent blood vessel position (that is, the large change quantity) may be calculated as the value of the characteristic WSS.

Thus, regarding the WSS in a direction not displayed on the screen at each position in the coronary artery, if the characteristic value exists, the WSS can be easily observed and therefore, occurrence of any important information being overlooked can be reduced.

First Modification

In the embodiment described above, the characteristic WSS in the coronary artery CT image at one time point is calculated at step 4. In a first modification to be described, the characteristic WSS is extracted from the coronary artery CT image at a plurality of time points.

In this case, the extracting function 145c extracts the value of the characteristic WSS on the basis of the result of comparing the WSS at the same position at the time points. Specifically, the extracting function 145c calculates the differential value among the WSS at the same position at the time points for the respective positions. Then, the extracting function 145c extracts the characteristic WSS on the basis of the differential value. More specifically, the extracting function 145c segments the blood vessel position (blood vessel region) where the differential value is larger than a threshold or the blood vessel position (blood vessel region) where the differential value is smaller than the threshold. The threshold may be determined in advance or a user can designate the threshold. In another example, the region with the maximum differential value or the region with the minimum differential value at the blood vessel wall intersecting with the cross section that is orthogonal to the center line of the blood vessel may be segmented for each position of the center line. That is to say, the extracting function 145c segments the region where the change of the WSS value is large or small in accordance with the time elapse.

Figure 4:
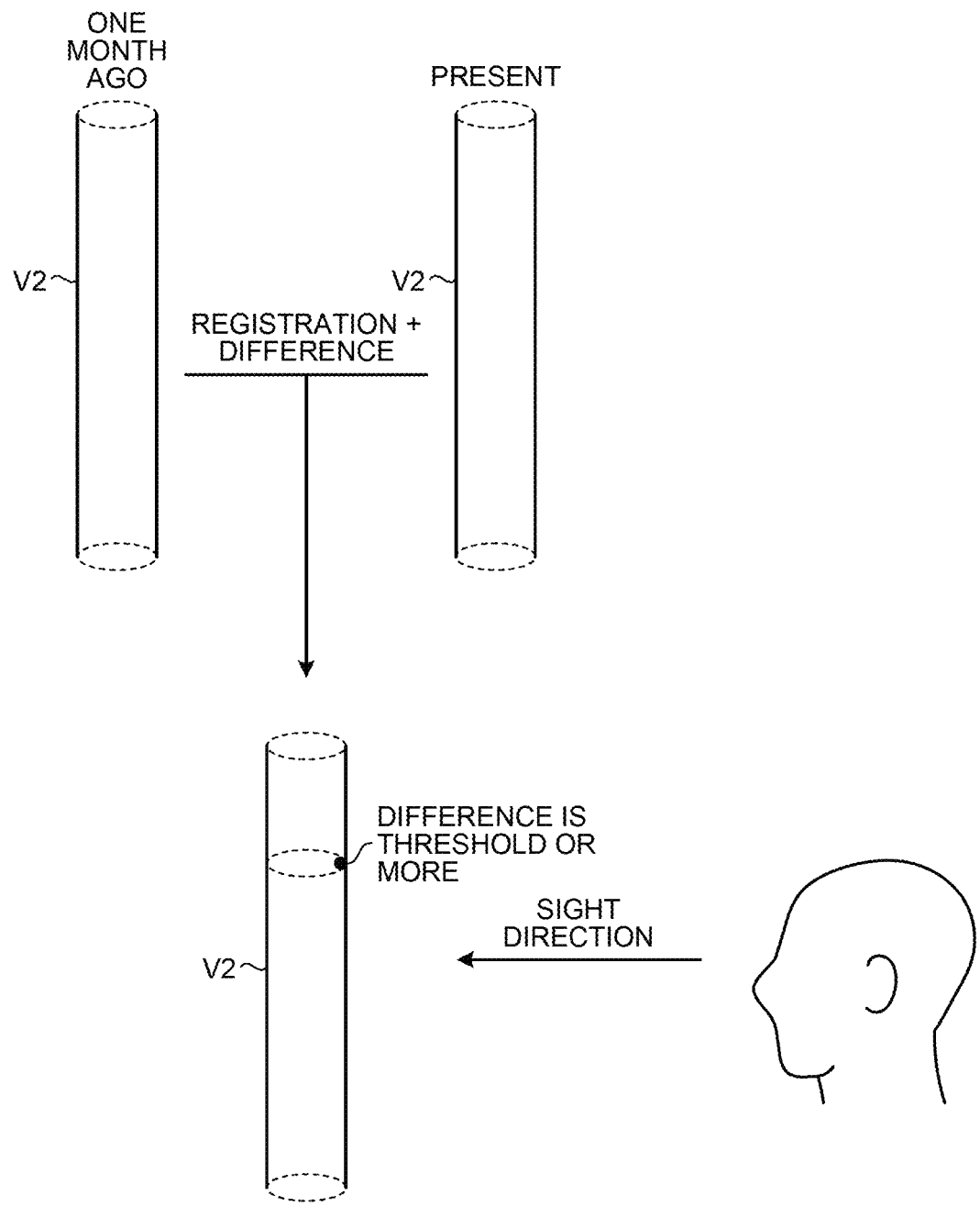
FIG. 4 is a diagram for describing one example of the extracting process and the display controlling process in the first embodiment.

FIG. 4 is a diagram for describing one example of the extracting process and the display controlling process in the first embodiment. As illustrated in FIG. 4, for example, the extracting function 145c performs a registration between the CT image of a coronary artery V2 collected a month ago and the CT image of the coronary artery V2 collected at present. The registration is performed by a known method. For example, a large deformation diffeomorphic metric mapping (LDDM) method or a free-form deformation (FFD) method can be used. Then, the extracting function 145c calculates the differential value of the WSS for each position using the WSS calculated by the calculating function 145b in each CT image. Here, the extracting function 145c segments the region where the differential value is more than or equal to the threshold. In addition, the extracting function 145c may segment the region with the maximum differential value or the region with the minimum differential value at the blood vessel wall intersecting with the cross section that is orthogonal to the center line of the blood vessel for each position of the center line.

The display controlling function 145e changes the display mode of the WSS in the blood vessel so that the value of the WSS in the segmented region is expressed in accordance with the user's instruction. For example, the display controlling function 145e performs the display of the current WSS at the blood vessel position where the differential value of the coronary artery V2 is the threshold or more on the side where the user can observe. Specifically, the display controlling function 145e specifies all the regions including the differential value that is more than or equal to the threshold at the blood vessel wall intersecting with the cross section that is orthogonal to the center line of the blood vessel for each position of the center line, and performs the display of the regions after arranging the regions so that the region with the larger differential value comes closer to the user's sight direction.

In addition, the display controlling function 145e can perform the display of the WSS by various other methods in the case of segmenting the region on the basis of the threshold. In one example, the display controlling function 145e specifies all the regions including the differential value that is more than or equal to the threshold at the blood vessel wall intersecting with the cross section that is orthogonal to the center line of the blood vessel for each position of the center line, and performs the display of the regions in the order of being closer to the sight direction. In another example, the display controlling function 145e specifies all the regions including the differential value that is more than or equal to the threshold at the blood vessel wall intersecting with the cross section that is orthogonal to the center line of the blood vessel for each position of the center line, and in the specified region, performs the display of the regions after arranging the regions so that the region with the higher WSS or the lower WSS at present comes closer to the user's sight direction. In still another example, the display controlling function 145e specifies all the regions including the differential value that is more than or equal to the threshold at the blood vessel wall intersecting with the cross section that is orthogonal to the center line of the blood vessel for each position of the center line, and in the specified region, performs the display of the regions after arranging alternately the regions with the high WSS and the regions with the low WSS at present.

In the case of segmenting the region with the maximum differential value or the region with the minimum differential value, the display controlling function 145e may perform the display of the current WSS corresponding to the maximum differential value or the minimum differential value on the side where the user can observe. Note that the value to be displayed may be not just the current WSS but may be the WSS in the past (in the modification, a month ago), or may be the differential value itself.

Moreover, regarding the region other than the characteristic region, not the map of the WSS but the map of the differential value may be displayed. In that case, the display controlling function 145e performs the display of a color image in which the color according to the differential value is mapped. Note that description is made of the case in which the difference is the threshold or more in the example in FIG. 4; however, the process is performed similarly when the difference is the threshold or less. By using the comparison result of the WSS calculated at the time points in this manner, the progress of the disease or the effect of the treatment can be checked.

Second Modification

In the embodiment described above, the arbitrary characteristic WSS value is calculated at step 4. In a second modification, the WSS is calculated by changing the characteristic condition (extraction criterion) for each blood vessel branch or each blood vessel region.

Specifically, the extracting function 145c calculates the representative value in the blood vessel on the basis of the extraction criterion determined for each region in accordance with the property of the blood vessel. For example, the extracting function 145c calculates the value of the relatively high WSS as the representative value about a region including plaque in the blood vessel, and calculates the value of the relatively low WSS as the representative value about a region not including the plaque in the blood vessel.

In this case, the extracting function 145c segments the plaque in the coronary artery first. For example, the extracting function 145c segments the position of the plaque for each blood vessel branch of the coronary artery by analyzing the coronary artery CT image of the subject. In one example, the extracting function 145c segments the position of the plaque from the information about the blood vessel diameter of the coronary artery. In another example, the extracting function 145c segments the position of the plaque by a threshold process using the coronary artery CT image. In still another example, the extracting function 145c may calculate the position of the plaque using a discriminator that has learned the characteristics of the distribution of the pixel values in the plaque by the technique of the machine learning.

Then, the extracting function 145c calculates the maximum value of the WSS as the representative value of the position where the plaque is segmented, and calculates the minimum value of the WSS as the representative value of the position where the plaque is not segmented, for example. This is based on the report that the low WSS is correlated with the risk of making the plaque progress and the high WSS is correlated with the risk of breaking the plaque. That is to say, about the region where the plaque already exists, the high WSS value is displayed so that the degree of the breaking risk can be predicted; on the other hand, about the region where the plaque does not exist, whether the plaque will be generated in the future can be predicted.

The display controlling function 145e changes the display mode of the WSS in the blood vessel so that the calculated representative value is expressed in accordance with the user's instruction. For example, the display controlling function 145e performs the display of the color image in which the color according to the representative value is mapped at the corresponding position in the blood vessel.

FIG. 5 is a diagram for describing one example of the extracting process and the display controlling process in the first embodiment. For example, the extracting function 145c segments the plaque in a coronary artery V3 by analyzing the coronary artery V3 as illustrated in the diagram in an upper part of FIG. 5. The extracting function 145c calculates, as the representative value, the maximum value among the WSS calculated at the respective positions in the blood vessel wall at the position where the plaque at each position in the blood vessel wall intersecting with the cross section that is orthogonal to the center line is segmented. In addition, the extracting function 145c calculates, as the representative value, the minimum value of the WSS calculated at the respective positions in the blood vessel wall at the position where the plaque at each position in the blood vessel wall intersecting with the cross section that is orthogonal to the center line is not segmented.

As illustrated in the diagram in a lower part of FIG. 5, the display controlling function 145e controls to perform the display of the maximum value of the WSS at the cross-sectional position where the plaque is segmented and the minimum value of the WSS at the cross-sectional position where the plaque is not segmented. For example, the display controlling function 145e performs the display of the color image where the color corresponding to the maximum value of WSS is mapped on the side where the user can observe in the region including the plaque in the VR image of the coronary artery V3 and the color corresponding to the minimum value of WSS is mapped on the side where the user can observe in the region not including the plaque in the VR image.

Here, the extracting function 145c can determine whether the plaque exists for each blood vessel branch in the blood vessel, and calculate the representative value for each blood vessel branch. That is to say, the extracting function 145c can cover the entire coronary arteries. In addition, the extracting function 145c can determine whether the plaque exists for each region along the extending direction of the blood vessel branch in the blood vessel, and calculate the representative value for each region along the extending direction of the blood vessel branch.

Moreover, in the case where the blood vessel includes the plaque, the extracting function 145c can perform the extracting process using the extraction criterion according to the hardness of the plaque. Specifically, the extracting function 145c determines the hardness of the plaque in the blood vessel further, and changes the extraction criterion in accordance with the hardness of the plaque.

As described above, the extracting function 145c calculates the relatively high WSS on the basis of the threshold about the region including the plaque; however, when the hardness of the segmented plaque is higher than the threshold, the threshold used to calculate the representative value is increased and when the hardness of the segmented plaque is lower than the threshold, the threshold used to calculate the representative value is decreased. This is because the presence of the high WSS region near the soft plaque causes a risk of breaking the plaque, and therefore, by decreasing the threshold when the soft plaque is segmented, even the lower value is easily segmented. Note that the hardness of the plaque may be based on the calcium score obtained by analyzing the coronary artery CT image.

Note that in the example described with reference to FIG. 5, the maximum WSS value is calculated about the cross-sectional position where the region including the plaque exists, and the minimum WSS value is calculated about the cross-sectional position where the region not including the plaque exists. However, the embodiment is not limited to this example, and the WSS higher than the threshold may be calculated about the cross-sectional position where the region including the plaque exists and the WSS lower than the threshold may be calculated about the cross-sectional position where the region not including the plaque exists.

In this case, the display controlling function 145e performs the display of the color image where the colors corresponding to a plurality of WSS values higher than the threshold are mapped on the side where the user can observe at the cross-sectional position in the VR image of the coronary artery V3 where the region including the plaque exists and the colors corresponding to a plurality of WSS values lower than the threshold are mapped on the side where the user can observe at the cross-sectional position in the VR image where the region not including the plaque exists. For example, the display controlling function 145e performs the display of the regions after arranging the regions so that the region with the larger WSS comes closer to the user's sight direction. That is to say, at the cross-sectional position where the region including the plaque exists, the regions may be displayed while being arranged so that the larger WSS comes closer to the user's sight direction, and at the cross-sectional position where the region not including the plaque exists, the regions may be displayed while being arranged so that the smaller WSS comes closer to the user's sight direction.

In the case of calculating the WSS on the basis of the threshold, the display controlling function 145e can perform the display of the WSS by various other methods. In one example, at the cross-sectional position in the VR image where the region including the plaque exists, the display controlling function 145e performs the display in the order that the position of the WSS higher than the threshold is closer to the user's sight direction, and at the cross-sectional position in the VR image where the region not including the plaque exists, performs the display in the order that the position of the WSS lower than the threshold is closer to the user's sight direction. In another example, the display controlling function 145e performs the display of, among the WSS values higher than the threshold, the high values and the low values alternately at the cross-sectional position in the VR image where the region including the plaque exists, and performs the display of, among the WSS values lower than the threshold, the high values and the low values alternately at the cross-sectional position in the VR image where the region not including the plaque exists.

The extracting function 145c can change the extraction criterion in accordance with the status of the myocardium. Specifically, the extracting function 145c further determines whether the myocardium, to which blood is supplied by the blood vessels, is inflamed, and if the myocardium is inflamed, the extracting function 145c changes the extraction criterion in the region not including the plaque in the blood vessel.

For example, the extracting function 145c determines whether the inflammation exists in a domination region of the myocardium that is dominated by the coronary artery to display the WSS. For example, the extracting function 145c specifies the domination region of the coronary artery to display the WSS from the coronary artery CT image including the myocardium using the existing algorithm such as a Voronoi method. Then, the extracting function 145c performs a registration between the myocardium SPECT image and the myocardium in the coronary artery CT image, and determines whether the specified domination region includes the inflammation.

Figure 6:
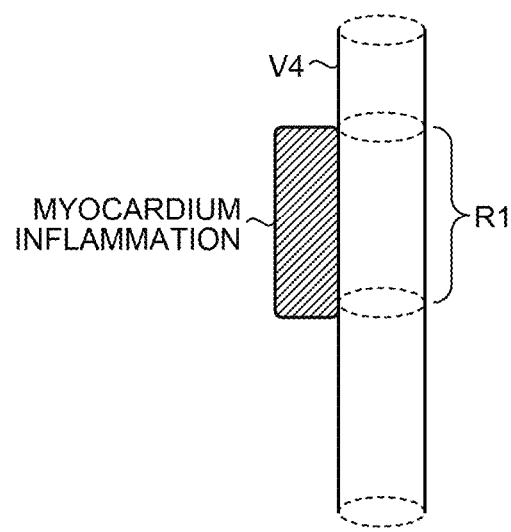
FIG. 6 is a diagram for describing one example of the extracting process and the display controlling process in the first embodiment.

Here, if the domination region includes the inflammation, the extracting function 145c changes the extraction criterion in the region not including the plaque in the blood vessel. FIG. 6 is a diagram for describing one example of the extracting process and the display controlling process in the first embodiment. For example, the extracting function 145c changes the extraction criterion for a region R1 not including the plaque in a coronary artery V4 including the myocardium inflammation in the domination region as illustrated in FIG. 6.

As described above, the extracting function 145c calculates the relatively low WSS value on the basis of the threshold in the region not including the plaque, and in the case where the myocardium is inflamed, the extracting function 145c increases the threshold used to calculate the representative value. This is because, in the case where the myocardium is inflamed, the plaque is easily formed, and therefore by increasing the threshold in the case where the myocardium is inflamed, the calculation is enabled even with the higher WSS value.

Third Modification

In the above embodiment, the display is switched so that the characteristic WSS value at each position where the center line is the axis comes to the front on the screen in accordance with the user's instruction at step 6. In a third modification, the display is switched for each blood vessel position.

For example, the extracting function 145c and the display controlling function 145e can perform the display of the calculated characteristic WSS value about each position along the center line of the blood vessel and also perform the display of only the value at a predetermined position on the front. For example, the display controlling function 145e may control so that only the WSS that is more than a predetermined threshold among the WSS at the respective positions along the center line is displayed to the user side.

Figure 7:
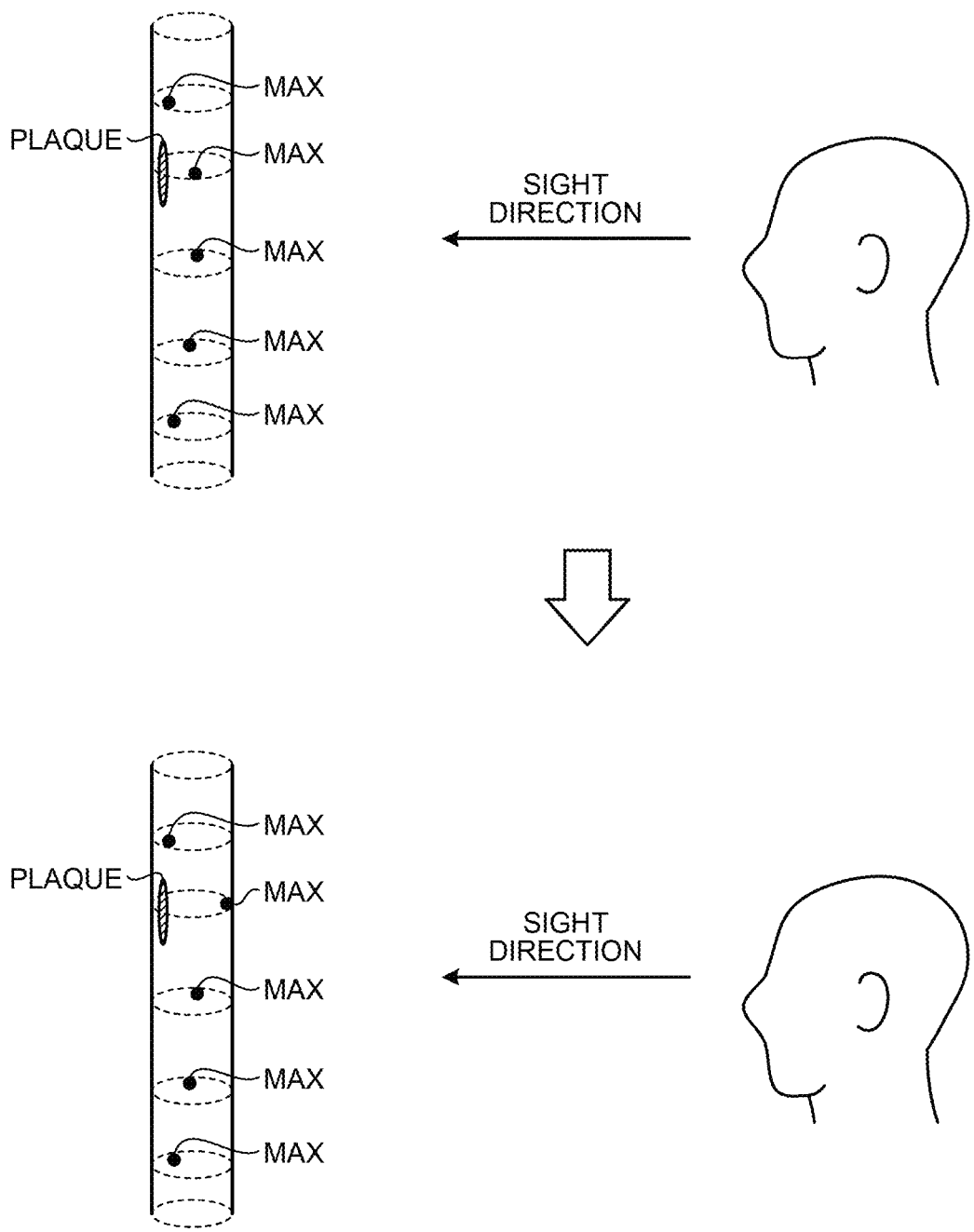
FIG. 7 is a diagram for describing one example of the extracting process and the display controlling process in the first embodiment.

The display controlling function 145e can switch the display on the basis of the position where the plaque exists. FIG. 7 is a diagram for describing one example of the extracting process and the display controlling process in the first embodiment. For example, the display controlling function 145e controls so that the maximum value of the WSS is displayed to the user side only about the position where the plaque exists as illustrated in FIG. 7.

In addition, the display controlling function 145e may control so that the maximum value, the minimum value, the average value of WSS, or the value of WSS with the largest difference from the adjacent value is displayed only about the position where the probability of the existence of the plaque is high, the position where the probability of the break of the plaque is high, or the position where the myocardium is inflamed.

Fourth Modification

In the embodiment described above, the WSS value is displayed at step 6. In a fourth modification, the extraction criterion of the characteristic WSS is displayed.

As described above, the medical image processing apparatus 140 calculates the representative value of the WSS on the basis of the extraction criterion that is determined in advance, and changes the display mode of the WSS on the basis of the extraction result (calculation result). Here, the display controlling function 145e can present the extraction criterion to the user. Specifically, the display controlling function 145e further performs the display of the extraction criterion used to calculate the representative value.

Figure 8:
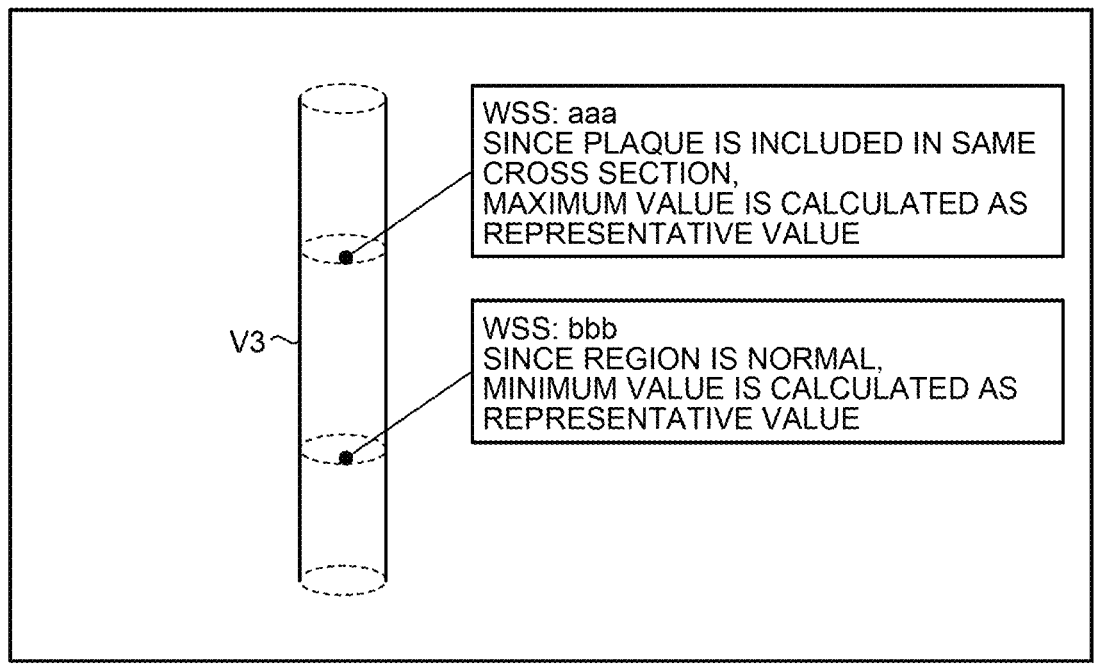
FIG. 8 is a diagram illustrating one example of the display of an extraction criterion in the first embodiment.

FIG. 8 is a diagram illustrating one example of the display of the extraction criterion in the first embodiment. As illustrated in FIG. 8, the display controlling function 145e performs the display of "WSS: aaa, since the plaque is included in the same cross section, the maximum value is calculated as the representative value" or "WSS: bbb, since the region is normal, the minimum value is calculated as the representative value" additionally in the display of the coronary artery V3. Thus, the user can find the value at each position in the blood vessel at a glance.

Figure 9:
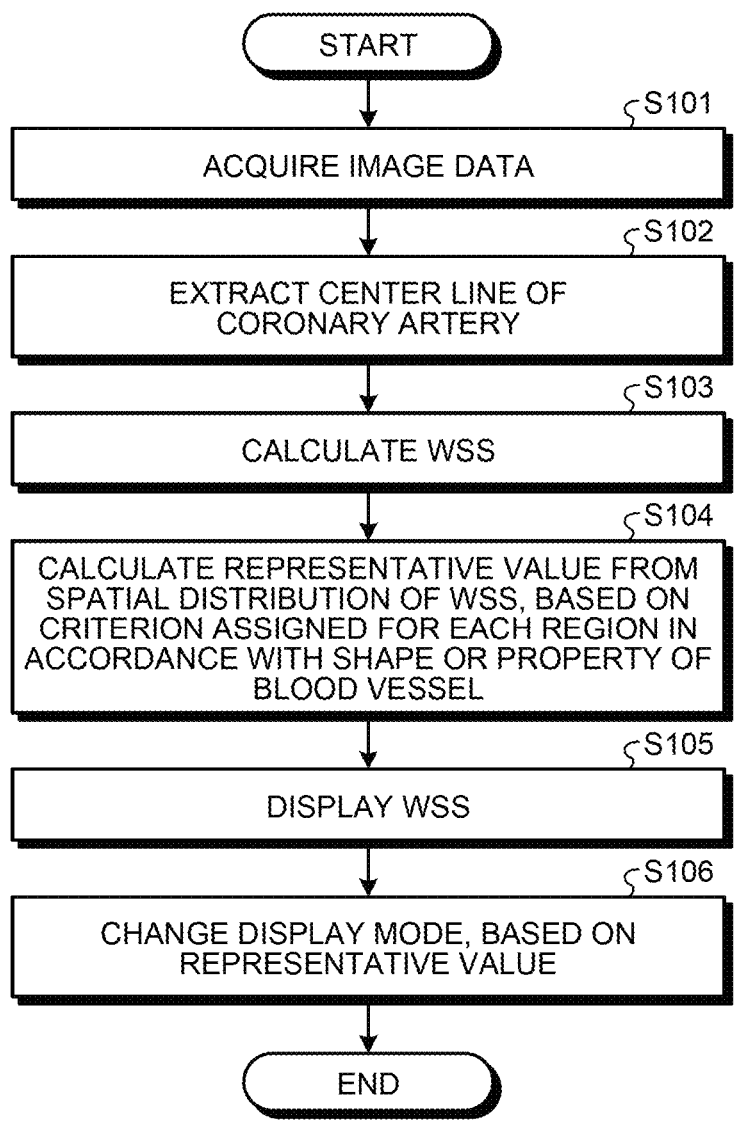
FIG. 9 is a flowchart illustrating the procedure of a process performed by each processing function of processing circuitry in the medical image processing apparatus according to the first embodiment.

Next, the procedure of the process in the medical image processing apparatus 140 is described with reference to FIG. 9. FIG. 9 is a flowchart illustrating the procedure of the process performed by each processing function of the processing circuitry 145 in the medical image processing apparatus 140 in the first embodiment.

For example, in the present embodiment, upon the reception of the user's instruction of starting the process through the input interface 143, the acquiring function 145a acquires the coronary artery CT image of the subject from the X-ray CT apparatus 110 or the medical image storage apparatus 120 (step S101) as illustrated in FIG. 9. This process is performed when, for example, the processing circuitry 145 calls the computer program corresponding to the acquiring function 145a from the memory 142 and executes the computer program.

Subsequently, the calculating function 145b extracts the center line of the coronary artery included in the coronary artery CT image of the subject acquired by the acquiring function 145a (step S102) and calculates the WSS on the basis of the coronary artery CT image (step S103). This process is performed when, for example, the processing circuitry 145 calls the computer program corresponding to the calculating function 145b from the memory 142 and executes the computer program.

Next, the extracting function 145c calculates the representative value from the spatial distribution of the WSS on the basis of the criterion assigned for each region on the basis of the shape or the property of the blood vessel (step S104). This process is performed when, for example, the processing circuitry 145 calls the computer program corresponding to the extracting function 145c from the memory 142 and executes the computer program.

Subsequently, the display controlling function 145e performs the display of the WSS calculated by the calculating function 145b (step S105) and changes the display mode on the basis of the representative value calculated by the extracting function 145c (step S106). This process is performed when, for example, the processing circuitry 145 calls the computer program corresponding to the display controlling function 145e from the memory 142 and executes the computer program.

As described above, in the first embodiment, the extracting function 145c extracts the blood vessel region or the representative value of the wall shear stress in the blood vessel on the basis of the extraction criterion determined for each region in accordance with the shape or the property of the blood vessel. The display controlling function 145e changes the display mode of the wall shear stress in the blood vessel on the basis of the result of extracting the representative value of the wall shear stress or the blood vessel region. Therefore, the medical image processing apparatus 140 according to the first embodiment can perform the display of the wall shear stress according to the extraction criterion, and enables the display that makes it easy to observe the wall shear stress.

In the first embodiment, the extracting function 145 c calculates the value of the relatively high wall shear stress as the representative value about the region including the plaque in the blood vessel, and calculates the value of the relatively low wall shear stress as the representative value about the region not including the plaque in the blood vessel. The display controlling function 145e changes the display mode of the wall shear stress in the blood vessel so that the calculated representative value is expressed. Therefore, the medical image processing apparatus 140 according to the first embodiment can perform the display of the value of the suitable wall shear stress for each of the region including the plaque and the region not including the plaque.

In the first embodiment, the extracting function 145c determines whether the plaque exists for each blood vessel branch in the blood vessel, and calculates the representative value for each blood vessel branch. In addition, the extracting function 145c determines whether the plaque exists for each region along the extending direction of the blood vessel branch in the blood vessel, and calculates the representative value for each region along the extending direction of the blood vessel branch. Therefore, the medical image processing apparatus 140 according to the first embodiment can calculate the suitable representative value.

In the first embodiment, the extracting function 145c additionally determines the hardness of the plaque in the blood vessel and changes the extraction criterion in accordance with the hardness of the plaque. Thus, the medical image processing apparatus 140 according to the first embodiment can perform the display of the value of the wall shear stress in consideration of the hardness of the plaque.

In the first embodiment, the extracting function 145c segments the blood vessel region in which the curvature of the blood vessel is higher than the threshold. The display controlling function 145e changes the display mode of the wall shear stress in the blood vessel so that the wall shear stress in the region inside the curve is expressed about the blood vessel region in which the curvature is higher than the threshold. Therefore, the medical image processing apparatus 140 according to the first embodiment can perform the display of the wall shear stress in the region inside the curve of the blood vessel region with the high curvature.

In addition, in the first embodiment, the extracting function 145c calculates the difference between the wall shear stresses at the same position calculated at the multiple time points for the same blood vessel, and segments the blood vessel region where the calculated difference is higher than the threshold or the blood vessel region where the calculated difference is lower than the threshold. The display controlling function 145e changes the display mode of the wall shear stress in the blood vessel so that the wall shear stress in the segmented blood vessel region is expressed. Therefore, the medical image processing apparatus 140 according to the first embodiment can perform the display of the value of the region where the wall shear stress exhibits the characteristic temporal change.

In the first embodiment, the extracting function 145c additionally determines whether the myocardium to which the blood is supplied by the blood vessel is inflamed, and if the myocardium is inflamed, the extracting function 145c changes the extraction criterion in the region not including the plaque in the blood vessel. Therefore, the medical image processing apparatus 140 according to the first embodiment can perform the display of the value of the wall shear stress in consideration of the inflammation of the myocardium.

In the first embodiment, moreover, the extracting function 145c calculates the maximum value, the minimum value, the average value, or the value with the largest difference from the adjacent value from among the values of the wall shear stress at the blood vessel wall intersecting with the cross section that is orthogonal to the center line of the blood vessel for each position of the center line. The display controlling function 145e changes the display mode of the wall shear stress in the blood vessel so that the maximum value, the minimum value, the average value, or the value with the largest difference that is calculated for each position of the center line of the blood vessel is expressed. Thus, the medical image processing apparatus 140 according to the first embodiment can perform the display of the value of the characteristic wall shear stress.

Moreover, in the first embodiment, the display controlling function 145e performs additional display of the extraction criterion used to segment the representative value or the blood vessel region. Therefore, the medical image processing apparatus 140 according to the first embodiment enables the user to find the displayed value of the wall shear stress.

Second Embodiment

In the first embodiment described above, the characteristic WSS value is calculated and displayed. In a second embodiment, the WSS value at the characteristic blood vessel position is displayed. Note that the medical image processing apparatus 140 according to the second embodiment is different from that of the first embodiment in the process content by the extracting function 145c and the display controlling function 145e. This different point is described mainly.

The extracting function 145c according to the second embodiment segments the characteristic blood vessel region in the blood vessel on the basis of the extraction criterion determined for each region in accordance with the shape of the blood vessel at step 4 described above. For example, the extracting function 145c segments the blood vessel region in which the curvature of the blood vessel is higher than the threshold. In this case, the extracting function 145c calculates the curvature at each position in the coronary artery. Then, the extracting function 145c segments the region where the calculated curvature is higher than a predetermined threshold, as the characteristic blood vessel region. Note that the entire coronary artery may be specified as the characteristic blood vessel position, or the position where the curvature is the largest or smallest in each blood vessel branch may be specified as the characteristic blood vessel position.

The display controlling function 145e performs the display of the value of the WSS at the characteristic blood vessel position. For example, the display controlling function 145e changes the display mode of the WSS in the blood vessel so that the WSS in the blood vessel region with the curvature higher than the threshold is expressed.

FIG. 10 is a diagram for describing one example of the extracting process and the display controlling process in the second embodiment. For example, as illustrated in the diagram in an upper part in FIG. 10, the extracting function 145c calculates the curvature for each position of the center line in a coronary artery V5, and by comparing the calculated curvature and the threshold, extracts a position P1 where the curvature is higher than the threshold. Then, the display controlling function 145e changes the display mode so that the user can observe the WSS value at the position P1 where the curvature is higher than the threshold as illustrated in the diagram in a lower part in FIG. 10. That is to say, the display controlling function 145e performs the display of the WSS value at the position P1 at the position, which is orthogonal to the center line, where the user can observe at the cross section of the blood vessel including the position P1.

For example, in the case of displaying the color image in which the color according to the WSS value is mapped on the VR image of the coronary artery V5, the display controlling function 145e performs the display of the color image in which the color according to the WSS value at the position P1 is mapped on the side where the user can observe on the cross section of the blood vessel that includes the position P1 and that is orthogonal to the center line of the coronary artery V5. In this case, the display controlling function 145e acquires the WSS values at all the positions of the blood vessel calculated by the calculating function 145b, and specifies the range the WSS can exist on the basis of the maximum value and the minimum value of the acquired WSS values. Then, the display controlling function 145e sets the color arrangement (color lookup table) for the specified range and maps the color according to the WSS value at the position P1 to the position P1 of the coronary artery V5.

Note that in FIG. 10, only the position P1 is illustrated as the region with the curvature higher than the threshold; however, in fact, all the positions where the curvature is higher than the threshold in the coronary artery V5 are extracted.

The extraction criterion according to the shape of the blood vessel may be employed not just in the case of segmenting the blood vessel region where the curvature is higher than the threshold but also in the case of segmenting the blood vessel region where the curvature is lower than the threshold. In this case, the display controlling function 145e may cause the display 144 to display, on the side where the user can observe on the cross section of the blood vessel including the position that is orthogonal to the center line and that has the curvature lower than the threshold, the value of the WSS at that position. Here, the threshold used to segment the region with the high curvature and the threshold used to segment the region with the low curvature may be set by different values.

The extraction criterion according to the shape of the blood vessel may use not just the curvature but also the blood vessel diameter. In this case, for example, the extracting function 145c may compare the blood vessel diameter and the threshold and segment the characteristic region on the basis of the comparison result. The segmentation according to the shape of the blood vessel may be performed for a particular blood vessel branch, or may be performed for the entire coronary arteries, that is, all the blood vessel branches.

The display controlling function 145e in the second embodiment performs the display with emphasis on the segmented blood vessel region at step 6 described above. For example, the display controlling function 145e performs the display with emphasis on the display object when displaying the WSS in the blood vessel region segmented by the extracting function 145c, for example the blood vessel region with the curvature higher than the threshold or the region including the plaque.

Figure 11:
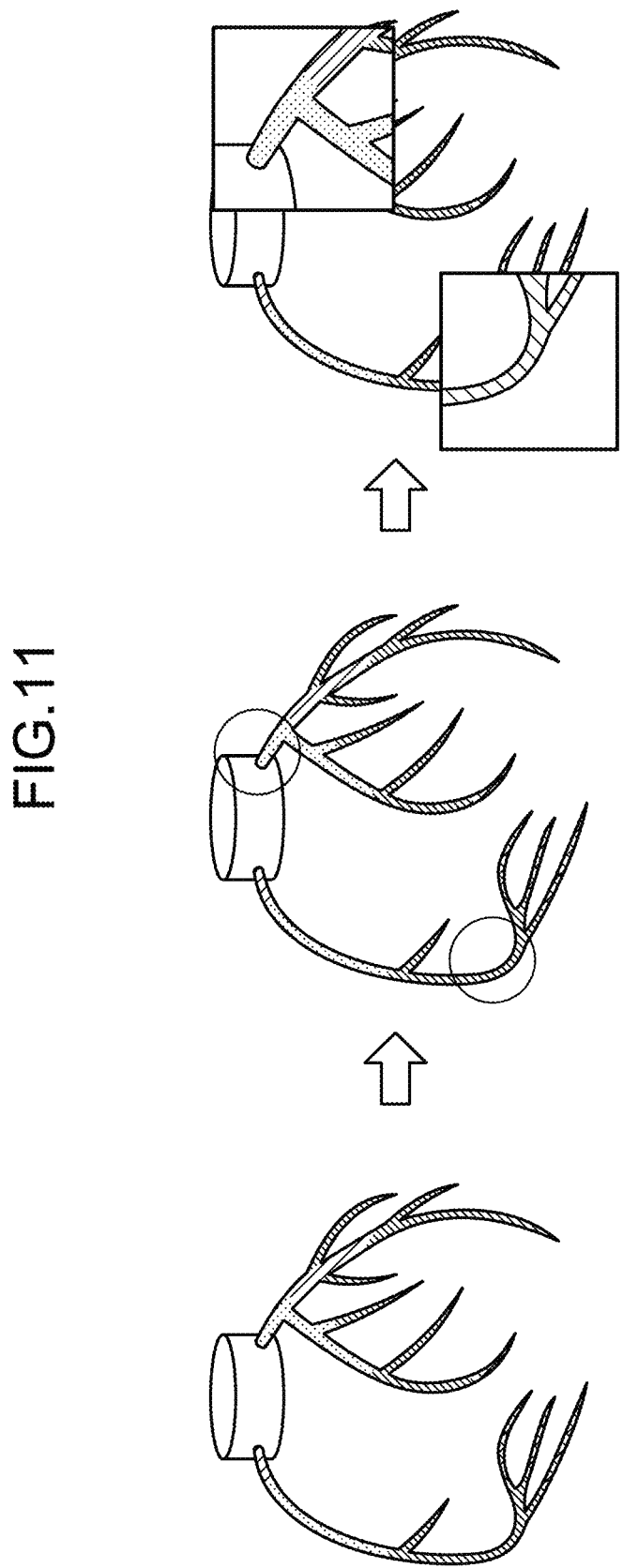
FIG. 11 is a diagram illustrating one example of the display controlling process in the second embodiment.
Figure 12:
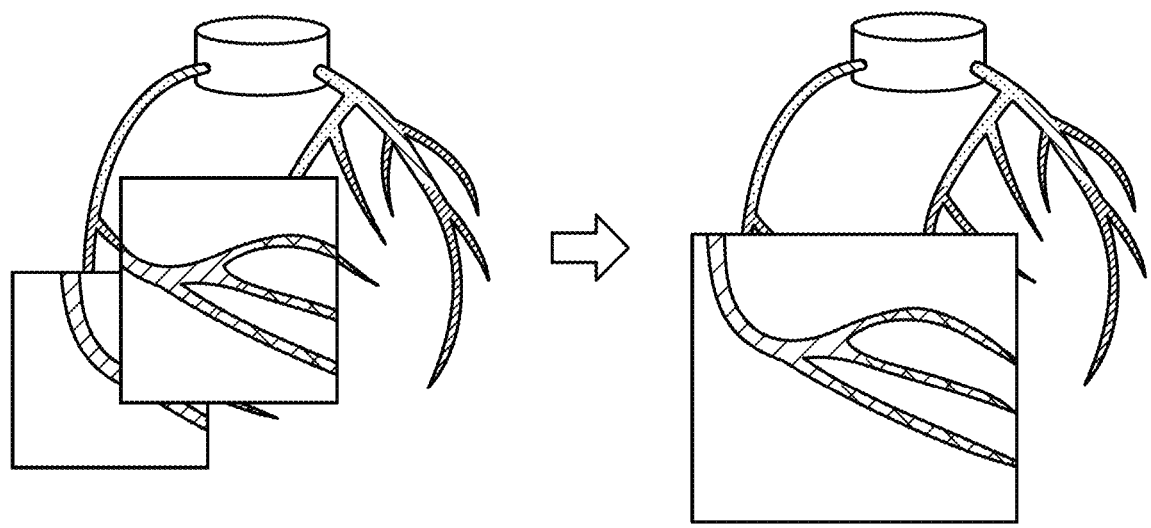
FIG. 12 is a diagram illustrating one example of the display controlling process in the second embodiment.
Figure 13:
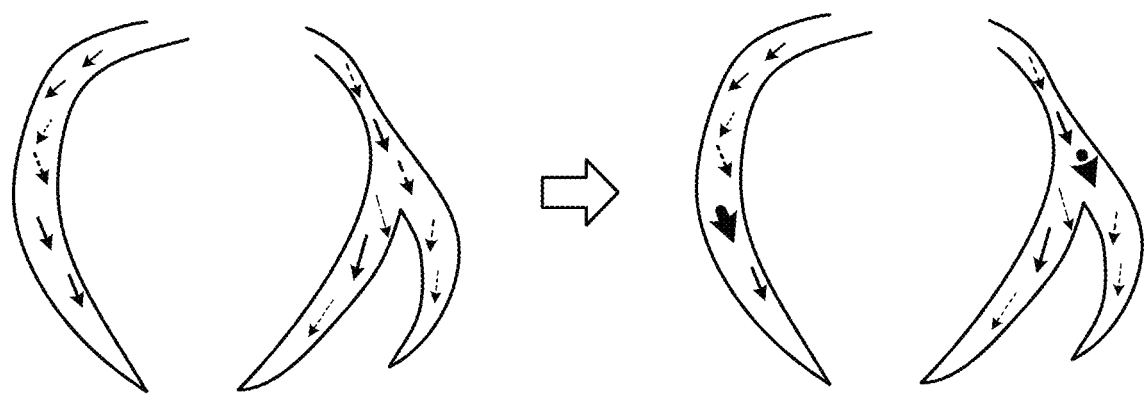
FIG. 13 is a diagram illustrating one example of the display controlling process in the second embodiment.

FIG. 11 to FIG. 13 each illustrate one example of the display controlling process in the second embodiment. For example, the display controlling function 145e emphasizes by changing the display mode of the segmented blood vessel region in accordance with the user's switching operation as illustrated in FIG. 11. For example, the display controlling function 145e emphasizes by displaying the information expressing the segmented blood vessel region (circle in the drawing) or by magnifying the segmented blood vessel region in accordance with the user's switching operation.

Here, in the case where the extracting function 145c segments a plurality of regions that are close to each other, magnifying each region may deteriorate the visibility. In view of this, in the case where the distance between the blood vessel regions to be magnified is smaller than a threshold, the display controlling function 145e magnifies the blood vessel regions in one magnifying region. For example, as illustrated in FIG. 12, in the case where the two regions that are segmented are close to each other and magnifying the regions results in the overlap, the display controlling function 145e magnifies one magnifying region including the two regions.

Note that the distance between the regions described above may be changed dynamically based on the magnifying ratio on the screen of the display image. In this case, the memory 142 stores the information expressing the relation between the magnifying ratio and the distance between the regions in advance. The display controlling function 145e reads out the information about the distance corresponding to the magnifying ratio of the region to be magnified, from the memory 142 and if the distance between the regions to be magnified is shorter than the read distance, the display controlling function 145e magnifies one magnifying region including the regions.

Note that the process of emphasizing the display object may be performed by any method that can emphasize the display object by changing the display mode of the WSS at the calculated positions. For example, the display controlling function 145e emphasizes the extracted representative value or blood vessel region using the color, texture, pattern, or additional information.

For example, the display controlling function 145e emphasizes the region using the color drastically different from the color in a color lookup table for assigning the color in accordance with the WSS value (for example, using black in the case of the general lookup table that changes blue to red, or using red in the case of grayscale). In addition, the display controlling function 145e can emphasize by changing the transmittance or gradation of the color.

In addition, in the case of expressing the WSS by texture, pattern, or the like (for example, expressing the WSS by the size of an arrow or a circle), the display controlling function 145e changes only the texture or pattern of the region to be emphasized. For example, in the case of expressing the value of WSS by the kind of the arrow as illustrated in FIG. 13, the display controlling function 145e changes the thickness of the arrow expressing the value of the WSS to be emphasized. Moreover, the display controlling function 145e can perform the display with emphasis by displaying a letter or a mark around the value of the WSS to be emphasized.

First Modification

In the second embodiment described above, the characteristic position is segmented based on the shape of the coronary artery at step 4. In a first modification, the characteristic position is segmented based on the diameter of the blood vessel or the property of the blood vessel.

In this case, for example, the extracting function 145c specifies the position where the plaque or calcification exists on the basis of the information about the blood vessel diameter or the like, and segments the specified position as the characteristic position. Moreover, the extracting function 145c calculates the probability of the break of the plaque by the machine learning technique or the like, specifies only the position where the plaque with high risk, such as plaque with the high probability of the break, exists, and segments the specified position as the characteristic position. Furthermore, the extracting function 145c specifies the position with the WSS whose change quantity from the WSS obtained from the coronary artery CT image in the past is the largest or smallest, and segments the specified position as the characteristic position. In addition, the extracting function 145c specifies the region with the inflammation on the basis of the distribution of the pixel values in the myocardium region around the coronary artery, and segments the position of the blood vessel included in the specified region as the characteristic position. In the case where another medical image such as a myocardium SPECT image proves that there is an inflamed region, a registration between the medical image and the coronary artery CT image specifies the inflamed region and the extracting function 145c segments the specified position as the characteristic position.

Second Modification

In the second embodiment, the value of the WSS at the characteristic position is displayed with emphasis at step 6. In a second modification, the characteristic position exists at a position where the visual recognition is difficult.

Figure 14:
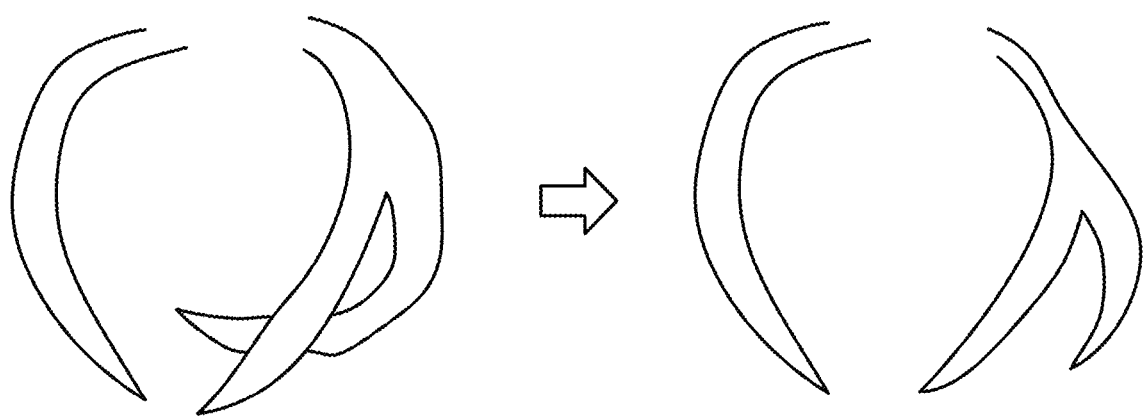
FIG. 14 is a diagram for describing one example of a process of deforming a blood vessel in the second embodiment.

For example, if another structure (for example, another blood vessel or heart) interrupts the observation of the blood vessel region that is emphasized, the display controlling function 145e may deform the blood vessel. FIG. 14 is a diagram for describing one example of a process of deforming the blood vessel in the second embodiment. For example, in the case of displaying the WSS in the blood vessels overlapping in the sight direction as illustrated in FIG. 14, the display controlling function 145e changes the shape of the blood vessels so that the blood vessels do not overlap in the sight direction and performs the display of the WSS at each blood vessel.

Note that the display controlling function 145e can deform the blood vessel by a stochastic method using a deformation model or the image processing technique, for example. The deformation of the blood vessel illustrated in FIG. 14 may be switched in accordance with the user's operation.

Third Modification

In the second embodiment, the value of the WSS at one characteristic position is displayed with emphasis at step 6. In a third modification, description is made of the case in which there are plurality of characteristic positions.

For example, in the case where there are a plurality of blood vessel regions to be emphasized, the display controlling function 145e can specify the observing direction where all or the most regions can be observed and switch the image to be displayed to the image in the specified direction.

Figure 15:
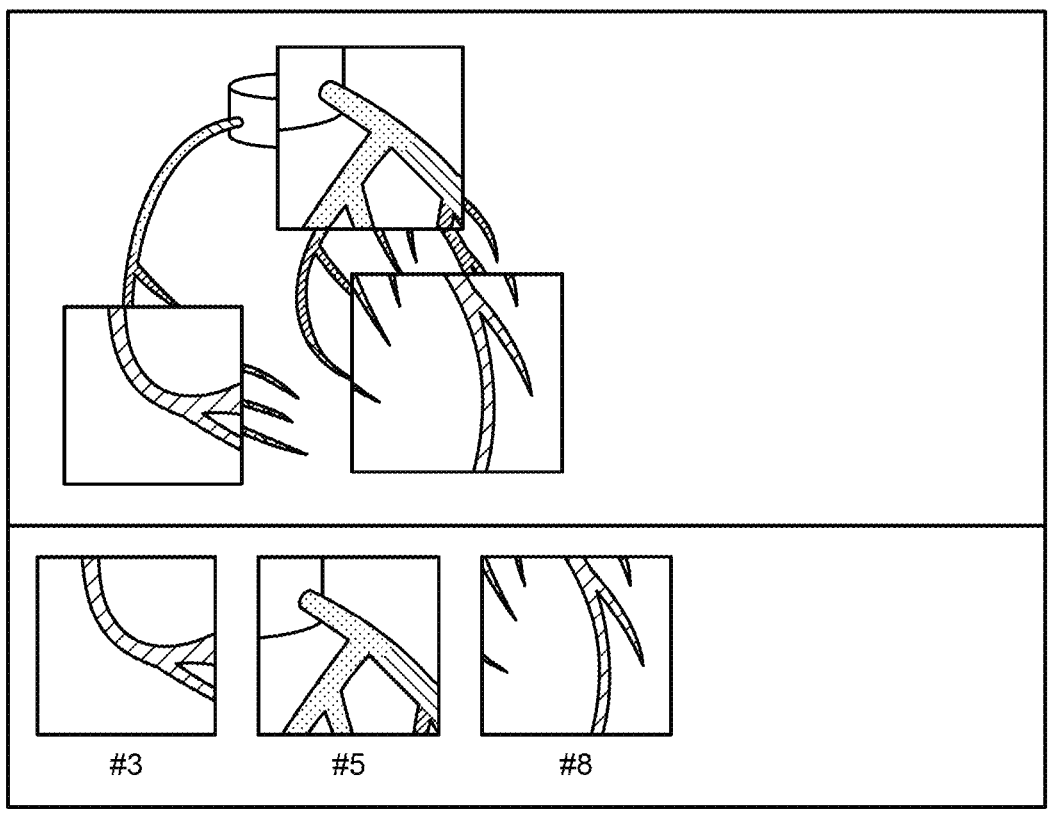
FIG. 15 is a diagram illustrating one example of the display controlling process in the second embodiment.

The display controlling function 145e can perform the display of the regions in a manner that the magnified region is disposed beside another region. That is to say, the display controlling function 145e performs the display by distinguishing the magnified representative value or blood vessel region from the blood vessel. FIG. 15 is a diagram illustrating one example of the display controlling process in the second embodiment. For example, the display controlling function 145e performs the display of the magnified blood vessel region in a display region different from the region where the entire coronary artery is displayed as illustrated in FIG. 15.

Here, the display controlling function 145e can perform the additional display of discrimination information for discriminating the blood vessel region that is displayed distinguishably. For example, the display controlling function 145e performs the display of the segment number (in the drawing, #3, #5, #8) defined by American Heart Association (AHA) for each of the blood vessel regions of the magnified coronary artery as illustrated in FIG. 15.

In addition, the display controlling function 145e may perform the display of only the WSS in the emphasized region. FIG. 16 is a diagram illustrating one example of the display controlling process in the second embodiment. For example, the display controlling function 145e controls so that only the magnified region is displayed as illustrated in FIG. 16. In this case, for example, the display controlling function 145e can perform such display by changing the color of the regions other than the magnified region to one color (for example, black) that is similar to the background color.

Fourth Modification

In the second embodiment, the value of the WSS at the characteristic position is displayed with emphasis at step 6. In a fourth modification, the medical image is displayed additionally.

For example, if the plaque or the like exists, just the magnified display of the VR image is not enough to see the force applied to the plaque in some cases. In view of this, the display controlling function 145e can perform the display in a manner that the cross-sectional image of the magnified blood vessel region is arranged in parallel. That is to say, the display controlling function 145e can perform the display in a manner that the WSS and the medical image expressing the cross section of the corresponding blood vessel are disposed in parallel.

Figure 17:
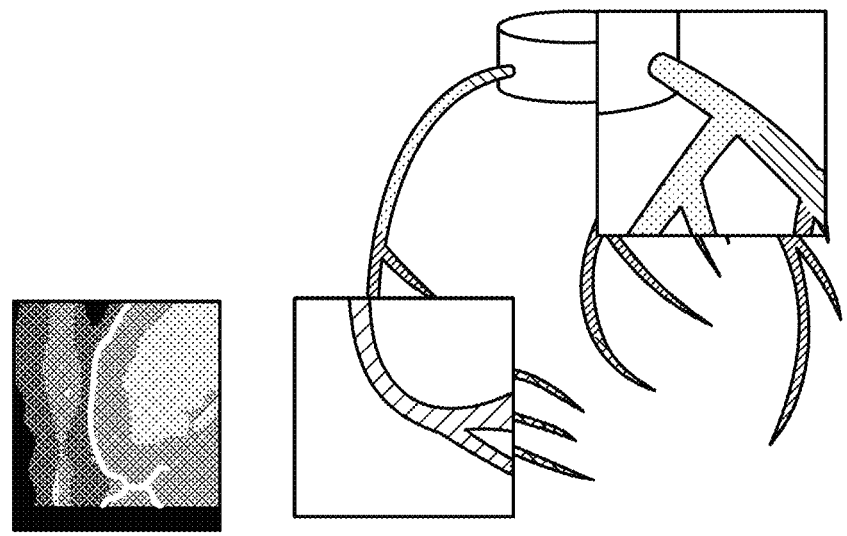
FIG. 17 is a diagram illustrating one example of the display controlling process in the second embodiment.

FIG. 17 is a diagram illustrating one example of the display controlling process in the second embodiment. For example, the display controlling function 145e can perform the display in a manner that the color image of the magnified blood vessel region and the MPR image showing the blood vessel region are disposed in parallel as illustrated in FIG. 17.

Here, the display controlling function 145e performs the display of the medical image where the cross section is changed in accordance with the shape or the property of the blood vessel region to be displayed. For example, the display controlling function 145e performs the display of the CPR image where the blood vessel region including the plaque is cut along the cross section where the blood vessel diameter is the shortest. In addition, the display controlling function 145e performs the display of the MPR image where the blood vessel region with the curvature higher than the threshold is cut along the cross section horizontal to the curve of the blood vessel.

Figure 18:
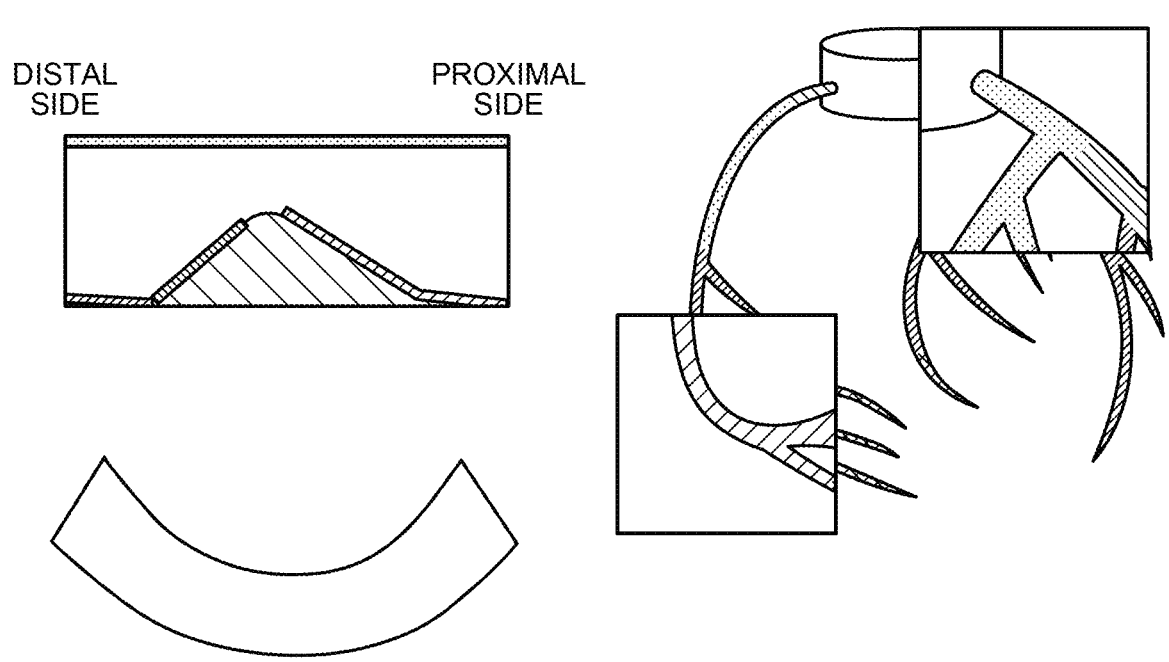
FIG. 18 is a diagram illustrating a display example of a schematic diagram of a blood vessel cross section in the second embodiment.

The display controlling function 145e can perform the display of a schematic diagram if the display of the cross-sectional image is difficult due to the limit of the resolution, for example. FIG. 18 is a diagram illustrating a display example of the schematic diagram of the blood vessel cross section in the second embodiment. For example, as illustrated in FIG. 18, the display controlling function 145e performs the display of the schematic diagram in the case where the blood vessel region is cut along the cross section where the blood vessel diameter is the shortest or the schematic diagram in the case where the blood vessel region is cut along the cross section horizontal to the curve of the blood vessel. Thus, since the tendency of the force applied to the plaque or the like can be observed even in the schematic diagram, the user can check the cross-sectional image with another screen when necessary.

Fifth Modification

In a fifth modification, the WSS is displayed in the stereoscopic view.

For example, the display controlling function 145e can perform the emphasized display of the blood vessel region using the stereoscopic view. By arranging the two VR images or the like, the user can obtain the visual of (can stereoscopically view) the image using the parallax of both eyes. In view of this, the display controlling function 145e changes the display mode of the region to be emphasized in only one of the two images that are arranged side by side, and thus the VR image in which the region is emphasized in the stereoscopic view is displayed. For example, the display controlling function 145e performs the display of the generated two VR images by rendering the blood vessel region that is displayed with emphasis from the position displaced by a parallax according to the stereoscopic view. Thus, the display controlling function 145e can perform the display of the image in which the blood vessel region is emphasized by the stereoscopic view.

As described above, the display controlling function 145e can display the extracted representative value or blood vessel region with emphasis in the second embodiment. Therefore, the medical image processing apparatus 140 according to the second embodiment enables the display of the highly visible information.

In the second embodiment, the display controlling function 145e can emphasize the extracted representative value or blood vessel region by magnification. Therefore, the medical image processing apparatus 140 according to the second embodiment enables the display of more visible information.

In the second embodiment, when the distance between the blood vessel regions to be magnified is smaller than the threshold, the display controlling function 145e magnifies the blood vessel regions in one magnifying region. Therefore, the medical image processing apparatus 140 according to the second embodiment enables the display of the image that makes it easy to observe the blood vessel regions.

In addition, in the second embodiment, the display controlling function 145e emphasizes the extracted representative value or blood vessel region using the color, texture, or additional information. Therefore, the medical image processing apparatus 140 according to the second embodiment enables the display with emphasis on the blood vessel region using various emphasizing methods.

In the second embodiment, in the case of displaying the wall shear stress in the blood vessels overlapping in the sight direction, the display controlling function 145e changes the shape of the blood vessels so that the blood vessels do not overlap in the sight direction and performs the display of the wall shear stress in each blood vessel. Therefore, the medical image processing apparatus 140 according to the second embodiment enables the checking of the information about the entire blood vessel at a glance.

In the second embodiment, the display controlling function 145e distinguishes the magnified representative value or blood vessel region from the blood vessel in the display. Therefore, the medical image processing apparatus 140 according to the second embodiment can increase the visibility of the magnified region further.

Moreover, in the second embodiment, the display controlling function 145e performs additional display of the discrimination information for discriminating the blood vessel region that is displayed distinguishably. Thus, the medical image processing apparatus 140 according to the second embodiment can provide the blood vessel information and perform the display about the blood vessel region more clearly.

In addition, in the second embodiment, the display controlling function 145e performs the display of the wall shear stress and the medical image expressing the cross section of the corresponding blood vessel in parallel. Thus, the medical image processing apparatus 140 according to the second embodiment can provide the mode information about the blood vessel region, and improve the diagnosis efficiency.

In the second embodiment, the display controlling function 145e performs the display of the medical image where the cross section is changed in accordance with the shape or the property of the blood vessel region to be displayed. Therefore, the medical image processing apparatus 140 according to the second embodiment can perform the display of the suitable medical image in accordance with the shape and the property of the blood vessel region.

Furthermore, in the second embodiment, the display controlling function 145e performs the display of the CPR image where the blood vessel region including the plaque is cut along the cross section where the blood vessel diameter is the shortest. The display controlling function 145e performs the display of the MPR image where the blood vessel region with the curvature higher than the threshold is cut along the cross section horizontal to the curve of the blood vessel. Therefore, the medical image processing apparatus 140 according to the second embodiment can perform the display of the suitable medical image.

Third Embodiment

In the first embodiment and the second embodiment described above, the information according to the value of the WSS is added to the blood vessel image in the display. In a third embodiment, the graph display of the WSS is described. Note that medical image processing apparatus 140 according to the third embodiment is different from that of the first embodiment and the second embodiment in the process content by the display controlling function 145e. This different point is mainly described below.

Figure 19:
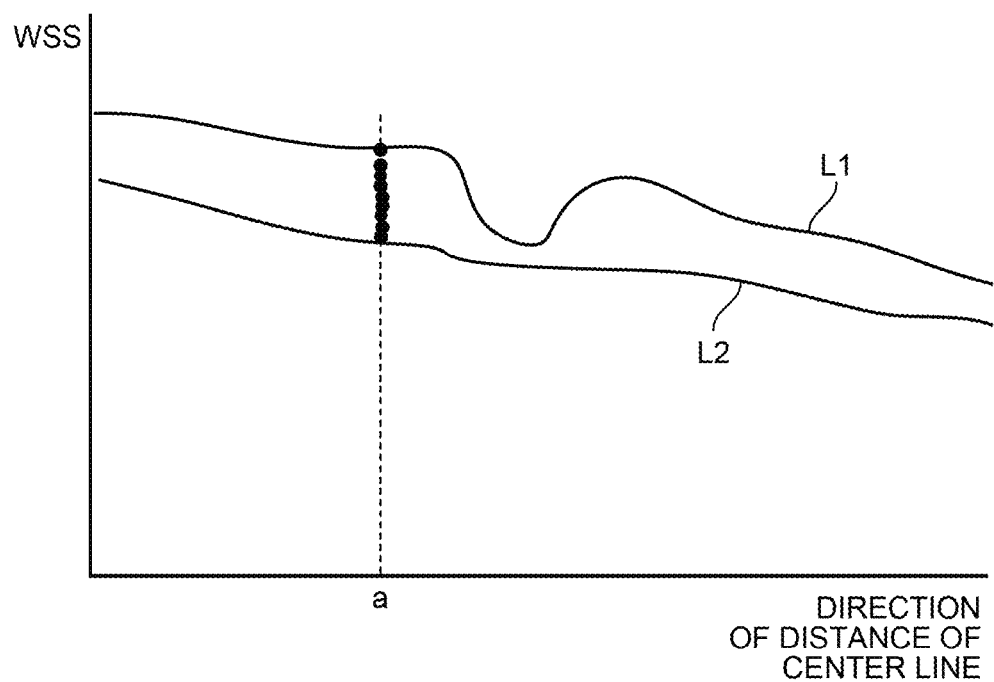
FIG. 19 is a diagram illustrating one example of the graph display in a third embodiment.

The display controlling function 145e according to the third embodiment performs additional display of a graph expressing the maximum value and the minimum value of the wall shear stress at the blood vessel wall intersecting with the cross section that is orthogonal to the center line of the blood vessel for each position of the center line. FIG. 19 is a diagram illustrating one example of the graph display in the third embodiment. For example, as illustrated in FIG. 19, the display controlling function 145e performs the display of the graph expressing the WSS values along the vertical axis and the position in the direction of the distance of the center line along the horizontal axis.

Here, the display controlling function 145e performs the display of the graph expressing a curve L1 representing the maximum value at each position and a curve L2 representing the minimum value at each position. Thus, the user can find the state of the maximum value and the minimum value of the WSS throughout the blood vessel at a glance.

The display controlling function 145e can perform the additional display of the distribution of the values of the WSS at the blood vessel wall intersecting with the cross section orthogonal to the center line on the graph. For example, as illustrated in FIG. 19, the display controlling function 145e plots and displays the distribution of the WSS at a position a of the blood vessel on the graph. Here, the position where the distribution of the WSS is displayed can be designated by the user arbitrarily. Thus, the user can find the distribution state of the WSS at a desired position in the blood vessel at a glance.

As described above, in the third embodiment, the display controlling function 145e performs the additional display of the graph expressing the maximum value and the minimum value of the wall shear stress at the blood vessel wall intersecting with the cross section that is orthogonal to the center line of the blood vessel for each position of the center line. Thus, the medical image processing apparatus 140 according to the third embodiment enables the user to find the state of the maximum value and the minimum value of the WSS at each position of the blood vessel at a glance.

In the third embodiment, the display controlling function 145e can perform the additional display of the distribution of the values of the wall shear stress at the blood vessel wall intersecting with the cross section orthogonal to the center line on the graph. Therefore, the medical image processing apparatus 140 according to the third embodiment enables the user to find the distribution state of the WSS in the blood vessel at a glance.

Fourth Embodiment

In a fourth embodiment, various other modes in the display of the WSS and the medical images are described. For example, the display controlling function 145e according to the fourth embodiment performs the display of the characteristic position of the WSS in a predetermined direction on the medical image expressing the cross section of the blood vessel. Here, the characteristic position of the WSS is, for example, the position with the relatively high WSS value, the position with the relatively low WSS value, the position exhibiting the value that may indicate the disease, or the position of the region including the plaque.

Figure 20:
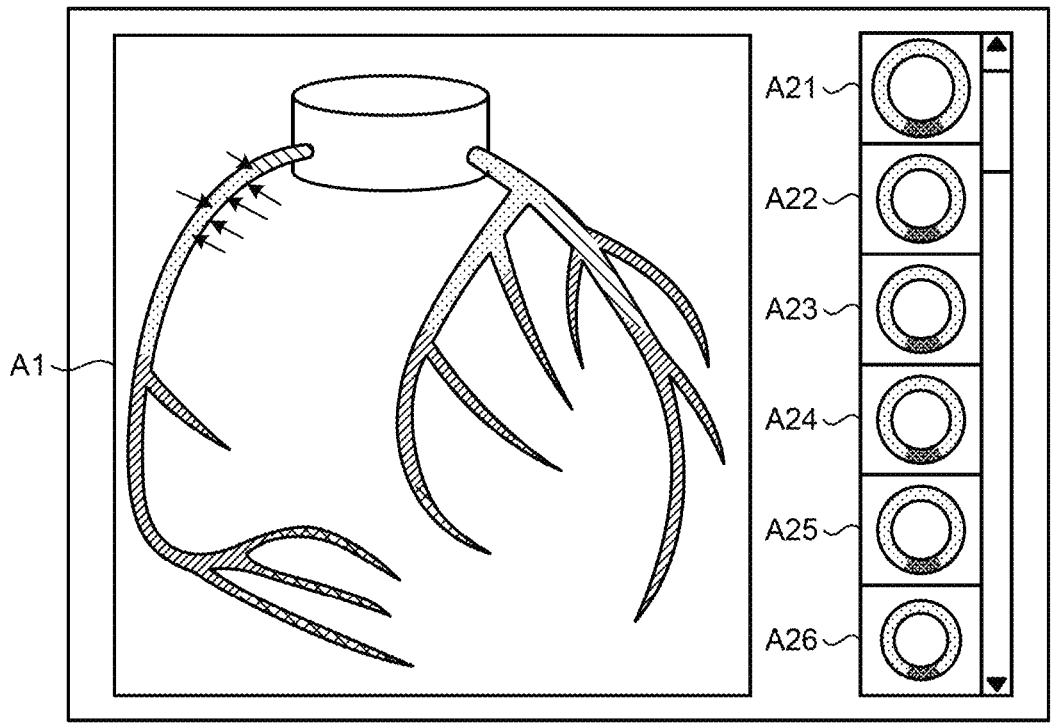
FIG. 20 is a diagram illustrating one example of a display controlling process in a fourth embodiment.

FIG. 20 is a diagram illustrating one example of the display controlling process in the fourth embodiment. In FIG. 20, a short axis plane image (crosscut image) expressing the cross section that is orthogonal to the center line of the blood vessel is displayed as the medical image expressing the cross section of the blood vessel. For example, as illustrated in FIG. 20, the display controlling function 145e performs the display of the VR image of the coronary artery in a display region A1 and the display of the short axis plane images at the respective positions of the coronary artery in display regions A21 to A26. Meanwhile, the display controlling function 145e can display an image in which each pixel of the short axis plane images are represented according to the WSS values corresponding to each pixel position. For example, the display controlling function 145e can display a color image in which each pixel of the short axis plane images are represented colors according to the WSS values. In addition, the display controlling function 145e may display an image represented by transparency, lightness, grayscale value, texture, symbol, mark and so on, according to the WSS values. Furthermore, the display controlling function 145e may display any images as long as it is an image represented by an expression method according to the WSS values.

Here, the display controlling function 145e performs the display of the characteristic position of the WSS in a predetermined direction in the short axis plane image. For example, as illustrated in FIG. 20, the display controlling function 145e performs the display of the characteristic position at each minor-axis cross section in a lower part of the short axis plane image. For example, the image generating function 145d generates the short axis plane image, in which a predetermined position in a circumferential direction of the coronary artery is the upper side, along the center line of the coronary artery. The display controlling function 145e compares the WSS at the respective positions in the circumferential direction of the coronary artery about the generated short axis plane image, and performs the display by rotating the short axis plane image using the image center as a rotation axis so that the characteristic position based on the comparison result comes to the lower side of the image.

Note that the position to be displayed in a predetermined direction in the short axis plane image is selected by the user arbitrarily. For example, the display controlling function 145e performs the display of GUI for the user to select the position to display in the predetermined direction in the short axis plane image, and the user selects the position to display in the predetermined direction by the operation of GUI through the input interface 143. The direction to display is not limited to the lower side of the short axis plane image illustrated in FIG. 20 and may be an arbitrary direction.

The display controlling function 145e can perform the display of the position on the three-dimensional image corresponding to the characteristic position of the WSS so that discrimination is possible. For example, the display controlling function 145e can indicate, with the arrow, the position on the VR image corresponding to the lower position of each short axis plane image displayed in the display regions A21 to A26 as illustrated in FIG. 20.

Additionally, the display controlling function 145e can perform the additional display of the information about the moving quantity of a medical image for displaying the characteristic position of the WSS in the predetermined direction in the medical image expressing the cross section of the blood vessel. As described above, the display controlling function 145e performs the display by rotating the short axis plane image using the image center as the rotation axis so that the characteristic position comes to a predetermined direction (for example, lower side) of the image. Thus, the display controlling function 145e can perform the additional display of the information about the rotation quantity as the moving quantity of the medical image.

For example, the display controlling function 145e changes the display mode of the frame of each display region in accordance with the rotation quantity of each short axis plane image displayed in the display regions A21 to A26 in FIG. 20. For example, the display controlling function 145e changes the color of the cuter frame of the display region A21 in accordance with the rotation quantity of each short axis plane image displayed in the display region A21. Similarly, the display controlling function 145e changes the color of the outer frame of the display regions A22 to A26 in accordance with the rotation quantity of the other short axis plane images. Furthermore, the display controlling function 145e can also perform the display of numerals expressing the rotation quantity in association with the display regions A21 to A26.

Figure 21:
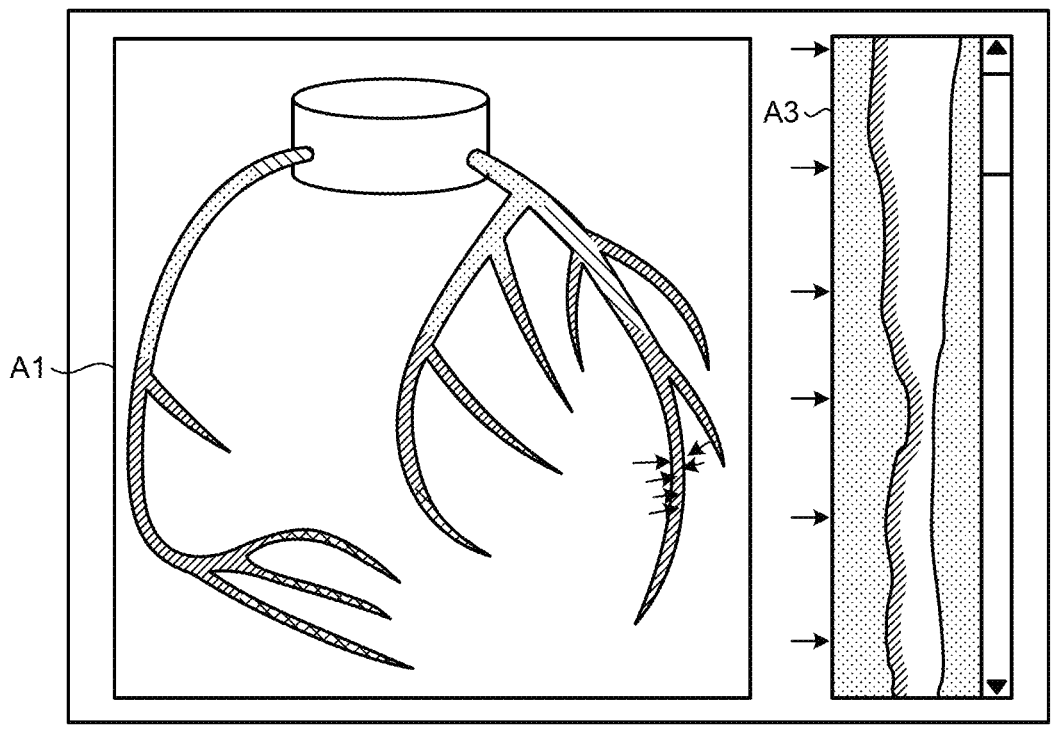
FIG. 21 is a diagram illustrating one example of the display controlling process in the fourth embodiment.

In the aforementioned examples, the short axis plane image is displayed as the medical image expressing the cross section of the blood vessel; however, the display controlling function 145e can alternatively perform the display of the CPR image as the medical image expressing the cross section of the blood vessel. FIG. 21 is a diagram illustrating one example of the display controlling process in the fourth embodiment. For example, the display controlling function 145e performs the display of the VR image of the coronary artery in the display region A1 and the CPR image of the coronary artery in a display region A3 as illustrated in FIG. 21.

Here, the display controlling function 145e can also perform the display of the characteristic position of the WSS in the predetermined direction in the medical image expressing the cross section of the blood vessel in the CPR image in a manner similar to the display of the short axis plane image. For example, as illustrated in FIG. 21, the display controlling function 145e performs the display of the characteristic position of the WSS on the left side in the CPR image of the coronary artery. That is to say, the image generating function 145d generates the CPR image where the cross-sectional direction of the blood vessel is changed so that the characteristic position of the WSS is in the predetermined direction (for example, left side) in the CPR image. Then, the display controlling function 145e performs the display of the generated CPR image. Note that the display controlling function 145e can perform the display of the CPR image as the color image with the color according to the value of the WSS. In addition, the characteristic position to be displayed in the predetermined direction and the direction to display are selected arbitrarily by the user.

The display controlling function 145e can perform the display of the positional relation between the images so that discrimination is possible, in a manner similar to the display of the short axis plane image. For example, the display controlling function 145e performs the display of the positional relation between the images by showing the arrows on the VR image and the CPR image as illustrated in FIG. 21.

Furthermore, the display controlling function 145e can perform the display of the information about the moving quantity of an image for expressing the characteristic position in the predetermined direction (for example, left side) in the image, in a manner similar to the display of the short axis plane image. For example, the display controlling function 145e changes the display mode of the frame of the display region A3 in accordance with the change quantity in the cross-sectional direction of the blood vessel for generating the CPR image in FIG. 21. For example, the display controlling function 145e changes the color of each position in the longitudinal direction of the outer frame of the display region A3 in accordance with the change quantity in the cross-sectional direction at each position in the extending direction of the blood vessel.

As described above, in the fourth embodiment, the display controlling function 145e performs the display of the characteristic position of the wall shear stress in the predetermined direction in the medical image expressing the cross section of the blood vessel. Therefore, the medical image processing apparatus 140 according to the fourth embodiment can easily discriminate the state of the continuity of the part in which the user is interested (characteristic position).

In the fourth embodiment, the display controlling function 145e performs the additional display of the information about the moving quantity of the medical image for displaying the characteristic position of the wall shear stress in the predetermined direction in the medical image expressing the cross section of the blood vessel. Therefore, the medical image processing apparatus 140 according to the fourth embodiment enables the user to find the distribution state of the characteristic positions easily. Here, in the above examples, the rotation quantity of the short axis plane image and the change quantity in the cross-sectional direction of the blood vessel for generating the CPR image are described, as the information about the moving quantity. However, the moving quantity is not limited to these examples, and may be any moving quantity for displaying the characteristic positions on the original image in a predetermined direction. For example, when the control is performed to display a characteristic position on the front side of the screen, which is easy to see, by changing an observation angle in the volume rendering image, the change quantity in the observation angle may be regarded as the moving quantity. Further, when the control is performed to display a characteristic position on the front side of the screen, which is easy to see, by rotating a predetermined blood vessel part along the blood vessel axis in the volume rendering image, the rotation quantity of the predetermined blood vessel part may be regarded as the moving quantity.

In addition, the display controlling function 145e in the fourth embodiment performs the display of the medical image expressing the cross section of the blood vessel and the three-dimensional image of the blood vessel, and the display of the position on the three-dimensional image corresponding to the characteristic position of the wall shear stress so that discrimination is possible. Accordingly, the medical image processing apparatus 140 according to the fourth embodiment enables the user to find the three-dimensional distribution state of the characteristic positions easily.

Other Embodiments

In the above embodiments, the coronary artery CT image is used as the medical image about the blood vessel in the heart; however, the embodiments are not limited to this example. For example, any kind of medical image based on which the shape of the blood vessel and the flow information including the flow rate of the blood can be calculated may be used. For example, the ultrasonic image obtained by the ultrasonic diagnosis image or the MR image obtained by the MRI apparatus may be used.

In the above embodiments, the information about the WSS is displayed on the display 144 of the medical image processing apparatus 140; however, the embodiments are not limited to this example. For example, the information about the WSS may be displayed on the display of the medical information display apparatus 130.

In the above embodiments, the extraction unit and the display control unit in this specification are achieved respectively by the extracting function and the display controlling function of the processing circuitry; however, the embodiments are not limited to this example. For example, the extraction unit and the display control unit in this specification that are achieved by the extracting function and the display controlling function of the processing circuitry as described in the embodiments may alternatively be achieved by hardware only, software only, or a combination of hardware and software.

The term "processor" used in the above embodiments mean, for example, a central processing unit (CPU), a graphics processing unit (GPU), an application specific integrated circuit (ASIC), a programmable logic device (for example, simple programmable logic device (SPLD)), a complex programmable logic device (CPLD), a field programmable gate array (FPGA), or the like. Here, instead of saving a computer program in the memory, the computer program may be directly incorporated in a circuit of the processor. In this case, the processor achieves the function by reading and executing the computer program incorporated in the circuit. Each processor in the present embodiment is not limited to the processor configured as one circuit for each processor, and a plurality of independent circuits may be combined into one processor to achieve that function.

Here, the computer program to be executed by the processor is provided by being incorporated in a read only memory (ROM), a storage circuit, or the like in advance. Note that this computer program may be stored in a computer-readable non-transitory storage medium such as a compact disc ROM (CD-ROM), a flexible disk (FD), a CD-recordable (CD-R), or a digital versatile disc (DVD) in a format that can be installed or executed in these devices. This computer program may be stored on a computer connected to the network such as the Internet, and provided or distributed by being downloaded through the network. For example, this computer program is configured by a module including each of the aforementioned processing functions. Regarding the actual hardware, a CPU reads out the computer program from the storage medium such as a ROM and executes the computer program, so that each module is loaded on a main storage device and generated on the main storage device.

In the aforementioned embodiments and modifications, the components of the devices in the drawings are conceptual in terms of function, and are not necessarily configured exactly as illustrated in the drawings in the physical point of view. That is to say, the specific mode of the dispersion or integration of the devices is not limited to the mode illustrated in the drawings, and a part of or all of the devices may be dispersed or integrated functionally or physically in an arbitrary unit in accordance with various loads, use circumstances, and the like. In addition, each processing function performed in each device can be achieved in an arbitrary part or entirely by the CPU and the computer program analyzed and executed in the CPU, or can be achieved as the hardware by wired logic.

Among the processes described in the aforementioned embodiments and modifications, all of or a part of the processes described as being performed automatically can be performed manually or all of or a part of the processes described as being performed manually can be performed automatically. In addition, the procedure of the process, the procedure of the control, the specific names, and the information including various data and parameters in the above description or the drawings can be changed arbitrarily unless stated otherwise.

According to at least one of the embodiments described above, the wall shear stress can be displayed so that the observation becomes easier.

Regarding the above embodiments, the following notes are disclosed as aspects and selective characteristics of the invention.

Note 1.

A medical image processing apparatus comprising:
an acquisition unit configured to acquire a distribution of wall shear stress of a blood vessel;
an extraction unit configured to extract a representative value or a blood vessel region from the distribution of the wall shear stress in the blood vessel, based on an extraction criterion determined for each region in accordance with a shape or a property of the blood vessel, and
a display control unit configured to change a display mode of the wall shear stress in the blood vessel, based on a result of extracting the representative value of the wall shear stress or a characteristic blood vessel region.

Note 2.

The extraction unit may calculate a value of relatively high wall shear stress as the representative value about a region including plaque in the blood vessel, and calculate a value of relatively low wall shear stress as the representative value about a region not including the plaque in the blood vessel, and
the display control unit may change the display mode of the wall shear stress in the blood vessel so as to express the calculated representative value.

Note 3.

The extraction unit may determine whether the plaque exists for each blood vessel branch of the blood vessel, and calculate the representative value for each blood vessel branch.

Note 4.

The extraction unit may determine whether the plaque exists for each region along an extending direction of a blood vessel branch of the blood vessel, and calculate the representative value for each region along the extending direction of the blood vessel branch.

Note 5.

The extraction unit may further determine hardness of the plaque in the blood vessel, and change the extraction criterion in accordance with the hardness of the plaque.

Note 6.

The extraction unit may segment a blood vessel region in which a curvature of the blood vessel is higher than a threshold, and
the display control unit may change the display mode of the wall shear stress in the blood vessel so as to express the wall shear stress in a region inside a curve about the blood vessel region in which the curvature is higher than the threshold.

Note 7.

The extraction unit may calculate a difference between the wall shear stresses at the same position calculated at a plurality of time points for the same blood vessel, and segment a blood vessel region in which the calculated difference is higher than a threshold or a blood vessel region in which the calculated difference is lower than the threshold, and the display control unit may change the display mode of the wall shear stress in the blood vessel so as to express the wall shear stress in the segmented blood vessel region.

Note 8.

The extraction unit may further determine whether a myocardium to which blood is supplied by the blood vessel is inflamed, and when the myocardium is inflamed, the extraction unit may change the extraction criterion in the region not including the plaque in the blood vessel.

Note 9.

The extraction unit may further be configured to calculate, for each position of a center line of the blood vessel, a maximum value, a minimum value, an average value, or a value with a largest difference from an adjacent value from among values of the wall shear stresses at a blood vessel wall intersecting with a cross section that is orthogonal to the center line, and the display control unit may additionally change the display mode of the wall shear stress in the blood vessel so as to express the maximum value, the minimum value, the average value, or the value with the largest difference from the adjacent value that is calculated for each position of the center line of the blood vessel.

Note 10.

The display control unit may perform additional display of the extraction criterion used to extract the representative value or the blood vessel region.

Note 11.

The display control unit may display the extracted representative value or blood vessel region with emphasis.

Note 12.

The display control unit may emphasize the extracted representative value or blood vessel region by magnification.

Note 13.

When a distance between a plurality of the blood vessel regions to be magnified is less than a threshold, the display control unit may magnify the blood vessel regions in one magnifying region.

Note 14.

The display control unit may emphasize the extracted representative value or blood vessel region using color, texture, a pattern, or additional information.

Note 15.

When displaying the wall shear stress in a plurality of the blood vessels overlapping in a sight direction, the display control unit may change a shape of the blood vessels so that the blood vessels do not overlap in the sight direction and to perform the display of the wall shear stress in each blood vessel.

Note 16.

The display control unit may distinguish the magnified representative value or blood vessel region from the blood vessel in the display.

Note 17.

The display control unit may perform additional display of discrimination information for discriminating the blood vessel region that is displayed distinguishably.

Note 18.

The display control unit may perform display of the wall shear stress and a medical image expressing a cross section of the corresponding blood vessel in parallel.

Note 19.

The display control unit may perform display of the medical image in which the cross section is changed in accordance with the shape or the property of the blood vessel region to be displayed.

Note 20.

The display control unit may perform display of a curved planar reconstruction (CPR) image where the blood vessel region including the plaque is cut along a cross section where a blood vessel diameter is shortest.

Note 21.

The display control unit may perform display of a multi planar reconstruction (MPR) image where the blood vessel region with a curvature higher than a threshold is cut along a cross section horizontal to a curve of the blood vessel.

Note 22.

The display control unit may perform additional display of a graph expressing a maximum value and a minimum value of the wall shear stress at a blood vessel wall intersecting with a cross section that is orthogonal to a center line of the blood vessel for each position of the center line.

Note 23.

The display control unit may perform additional display of the distribution of the values of the wall shear stress at the blood vessel wall intersecting with the cross section orthogonal to the center line on the graph.

Note 24.

The display control unit may perform display of a characteristic position of the wall shear stress in a predetermined direction in a medical image expressing a cross section of the blood vessel.

Note 25.

The display control unit may perform additional display of information about a moving quantity of the medical image for expressing the characteristic position of the wall shear stress in a predetermined direction in the medical image expressing the cross section of the blood vessel.

Note 26.

The display control unit may perform display of the medical image expressing the cross section of the blood vessel and a three-dimensional image of the blood vessel, and also display of a position on the three-dimensional image corresponding to the characteristic position of the wall shear stress so that discrimination is possible.

Note 27.

A medical image processing apparatus comprising: an extraction unit configured to extract a representative value or a blood vessel region, based on a spatial distribution of wall shear stress in a blood vessel; and a display control unit configured to change a display mode of the wall shear stress in the blood vessel, based on a result of extracting the representative value of the wall shear stress or the blood vessel region.

Note 28.

A medical image processing system comprising a medical image processing apparatus and a medical information display apparatus, wherein the medical image processing apparatus is configured to
  acquire a distribution of wall shear stress of a blood vessel, and
  extract a representative value or a characteristic blood vessel region from the distribution of the wall shear stress in the blood vessel, based on an extraction criterion determined for each region in accordance with a shape or a property of the blood vessel, and the medical information display apparatus is configured to change a display mode of the wall shear stress in the blood vessel, based on a result of extracting the representative value of the wall shear stress or the blood vessel region.

Note 29.

A medical image processing method comprising:

acquiring a distribution of wall shear stress of a blood vessel;

extracting a representative value or a blood vessel region from the distribution of the wall shear stress in the blood vessel, based on an extraction criterion determined for each region in accordance with a shape or a property of the blood vessel; and changing a display mode of the wall shear stress in the blood vessel, based on a result of extracting the representative value of the wall shear stress or a characteristic blood vessel region.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
processing circuitry configured to
    acquire a distribution of wall shear stress of a blood vessel,
    select a representative value from all values of the wall shear stress at 360 degrees in a horizontally cross-sectional direction in which a center line of the blood vessel is an axis, the representative value being selected at each position of the center line of the blood vessel, based on an extraction criterion determined for each region in accordance with a shape or a property of the blood vessel, and
    change a display mode of the wall shear stress in the blood vessel, based on a result of selecting the representative values of the wall shear stress or a characteristic blood vessel region.

2. The medical image processing apparatus according to claim 1, wherein the processing circuitry is further configured to:
    calculate a value of a relatively high wall shear stress as the representative value about a region including plaque in the blood vessel, and calculate a value of a relatively low wall shear stress as the representative value about a region not including the plaque in the blood vessel, and
    change the display mode of the wall shear stress in the blood vessel so as to express the calculated representative values.

3. The medical image processing apparatus according to claim 2, wherein the processing circuitry is further configured to determine whether the plaque exists for each blood vessel branch of the blood vessel, and calculate the representative values for each blood vessel branch.

4. The medical image processing apparatus according to claim 2, wherein the processing circuitry is further configured to determine whether the plaque exists for each region along an extending direction of a blood vessel branch of the blood vessel, and calculate the representative values for each region along the extending direction of the blood vessel branch.

5. The medical image processing apparatus according to claim 2, wherein the processing circuitry is further configured to determine hardness of the plaque in the blood vessel, and change the extraction criterion in accordance with the hardness of the plaque.

6. The medical image processing apparatus according to claim 2, wherein the processing circuitry is further configured to determine whether a myocardium to which blood is supplied by the blood vessel is inflamed, and when the myocardium is inflamed, the processing circuitry is further configured to change the extraction criterion in the region not including the plaque in the blood vessel.

7. The medical image processing apparatus according to claim 1, wherein the processing circuitry is further configured to:
    segment a blood vessel region in which a curvature of the blood vessel is higher than a threshold, and
    change the display mode of the wall shear stress in the blood vessel so as to express the wall shear stress in a region inside a curve about the blood vessel region in which the curvature is higher than the threshold.

8. The medical image processing apparatus according to claim 1, wherein the processing circuitry is further configured to:
    calculate a difference between the wall shear stresses at a same position calculated at a plurality of time points for a same blood vessel, and segment a blood vessel region in which the calculated difference is higher than a threshold or a blood vessel region in which the calculated difference is lower than the threshold, and
    change the display mode of the wall shear stress in the blood vessel so as to express the wall shear stress in the segmented blood vessel region.

9. The medical image processing apparatus according to claim 1, wherein the processing circuitry is further configured to:
    calculate, for each position of the center line of the blood vessel, a maximum value, a minimum value, an average value, or a value with a largest difference from an adjacent value from among values of the wall shear stresses at a blood vessel wall intersecting with a cross section that is orthogonal to the center line, and
    additionally change the display mode of the wall shear stress in the blood vessel so as to express the maximum value, the minimum value, the average value, or the value with the largest difference from the adjacent value that is calculated for each position of the center line of the blood vessel.

10. The medical image processing apparatus according to claim 1, wherein the processing circuitry is further configured to perform additional display of the extraction criterion used to extract the representative values or a blood vessel region.

11. The medical image processing apparatus according to claim 1, wherein the processing circuitry is further configured to display the extracted representative values or a blood vessel region with emphasis.

12. The medical image processing apparatus according to claim 11, wherein the processing circuitry is further configured to emphasize the extracted representative values or the blood vessel region by magnification.

13. The medical image processing apparatus according to claim 12, wherein when a distance between a plurality of the blood vessel regions to be magnified is less than a threshold, the processing circuitry is further configured to magnify the blood vessel regions in one magnifying region.

14. The medical image processing apparatus according to claim 12, wherein the processing circuitry is further configured to distinguish the magnified representative values or the blood vessel region from the blood vessel in the display.

15. The medical image processing apparatus according to claim 14, wherein the processing circuitry is further configured to perform additional display of discrimination information for discriminating the blood vessel region that is displayed distinguishably.

16. The medical image processing apparatus according to claim 11, wherein the processing circuitry is further configured to emphasize the extracted representative values or the blood vessel region using a color, a texture, a pattern, or additional information.

17. The medical image processing apparatus according to claim 1, wherein when displaying the wall shear stress in a plurality of the blood vessels overlapping in a sight direction, the processing circuitry is further configured to change a shape of the blood vessels so that the blood vessels do not overlap in the sight direction and perform the display of the wall shear stress in each blood vessel.

18. The medical image processing apparatus according to claim 1, wherein the processing circuitry is further configured to perform display of the wall shear stress and a medical image expressing a cross section of the corresponding blood vessel in parallel.

19. The medical image processing apparatus according to claim 18, wherein the processing circuitry is further configured to perform display of the medical image in which the cross section is changed in accordance with the shape or the property of the blood vessel region to be displayed.

20. The medical image processing apparatus according to claim 19, wherein the processing circuitry is further configured to perform display of a curved planar reconstruction image where the blood vessel region including plaque is cut along a cross section where a blood vessel diameter is shortest.

21. The medical image processing apparatus according to claim 19, wherein the processing circuitry is further configured to perform display of a multi-planar reconstruction image where the blood vessel region with a curvature higher than a threshold is cut along a cross section horizontal to a curve of the blood vessel.

22. The medical image processing apparatus according to claim 1, wherein the processing circuitry is further configured to perform additional display of a graph expressing a maximum value and a minimum value of the wall shear stress at a blood vessel wall intersecting with a cross section that is orthogonal to the center line of the blood vessel for each position of the center line.

23. The medical image processing apparatus according to claim 22, wherein the processing circuitry is further configured to perform additional display of the plurality of the values of the wall shear stress at the blood vessel wall intersecting with the cross section orthogonal to the center line on the graph.

24. The medical image processing apparatus according to claim 1, wherein the processing circuitry is further configured to perform display of a characteristic position of the wall shear stress in a predetermined direction in a medical image expressing a cross section of the blood vessel.

25. The medical image processing apparatus according to claim 24, wherein the processing circuitry is further configured to perform additional display of information about a moving quantity of the medical image for expressing the characteristic position of the wall shear stress in a predetermined direction in the medical image expressing the cross section of the blood vessel.

26. The medical image processing apparatus according to claim 24, wherein the processing circuitry is further configured to perform display of the medical image expressing the cross section of the blood vessel and a three-dimensional image of the blood vessel, and perform display of a position on the three-dimensional image corresponding to the characteristic position of the wall shear stress so that discrimination is possible.

27. A medical image processing apparatus, comprising:
processing circuitry configured to
select a representative value from all values of wall shear stress at 360 degrees in a horizontally cross-sectional direction in which a center line of a blood vessel is an axis, the representative value being selected at each position of the center line of the blood vessel, based on a spatial distribution of the wall shear stress in the blood vessel, and
change a display mode of the wall shear stress in the blood vessel, based on a result of selecting the representative values of the wall shear stress or a characteristic blood vessel region.

28. A medical image processing system, comprising:
a medical image processing apparatus including first processing circuitry; and
a medical information display apparatus including second processing circuitry, wherein
the first processing circuitry is configured to
acquire a distribution of wall shear stress of a blood vessel, and
select a representative value from all values of the wall shear stress at 360 degrees in a horizontally cross-section direction in which a center line of the blood vessel is an axis, the representative value being selected at each position of the center line of the blood vessel, based on an extraction criterion determined for each region in accordance with a shape or a property of the blood vessel, and
the second processing circuitry is configured to change a display mode of the wall shear stress in the blood vessel, based on a result of selecting the representative values of the wall shear stress or a characteristic blood vessel region.

29. A medical image processing method, comprising:
acquiring a distribution of wall shear stress of a blood vessel;
selecting a representative value from all values of the wall shear stress at 360 degrees in a horizontally cross-section direction in which a center line of the blood vessel is an axis, the representative value being selected at each position of the center line of the blood vessel, based on an extraction criterion determined for each region in accordance with a shape or a property of the blood vessel; and
changing a display mode of the wall shear stress in the blood vessel, based on a result of selecting the representative values of the wall shear stress or a characteristic blood vessel region.

* * * * *